(12) United States Patent
MacDonald et al.

(10) Patent No.: US 7,280,441 B2
(45) Date of Patent: Oct. 9, 2007

(54) VISUAL INDICATOR CHRONOGRAPH AND THE USE OF THE SAME

(75) Inventors: John Gavin MacDonald, Decatur, GA (US); Kelly D. Arehart, Alpharetta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 267 days.

(21) Appl. No.: 11/000,234

(22) Filed: Nov. 30, 2004

(65) Prior Publication Data

US 2006/0114754 A1    Jun. 1, 2006

(51) Int. Cl.
  *G04F 1/00*     (2006.01)
  *A61F 13/20*    (2006.01)
  *G01D 21/00*    (2006.01)

(52) U.S. Cl. .................. 368/327; 116/206; 604/361

(58) Field of Classification Search ............ 368/327, 368/114; 604/361; 116/206, 200; 374/102
  See application file for complete search history.

(56) References Cited

U.S. PATENT DOCUMENTS

| | | | |
|---|---|---|---|
| 2,156,880 | A | 5/1939 | Slomon |
| 3,414,415 | A | 12/1968 | Broad, Jr. |
| 3,480,402 | A | 11/1969 | Jackson |
| 3,520,124 | A | 7/1970 | Myers |
| 4,229,813 | A | 10/1980 | Lilly et al. |
| 4,292,916 | A | 10/1981 | Bradley et al. |
| 4,643,122 | A | 2/1987 | Seybold |
| 4,824,827 | A | 4/1989 | Kelly et al. |
| 4,903,254 | A | 2/1990 | Haas |
| 5,036,859 | A | 8/1991 | Brown |
| 5,045,283 | A | 9/1991 | Patel |
| 5,053,339 | A | 10/1991 | Patel |
| 5,058,088 | A | 10/1991 | Haas et al. |
| 5,107,470 | A | 4/1992 | Pedicano et al. |
| 5,322,031 | A | 6/1994 | Lerner et al. |

(Continued)

FOREIGN PATENT DOCUMENTS

EP    0813850 A2    12/1997

(Continued)

OTHER PUBLICATIONS

"Fatty Acids", http://www.cyberlipid.org/fa/acid0001.htm, viewed and printed Feb. 3, 2005, pp. 1-15.

(Continued)

*Primary Examiner*—Vit Miska
*Assistant Examiner*—Sean Kayes
(74) *Attorney, Agent, or Firm*—Vincent T. Kung

(57) ABSTRACT

A timer indicator or chronograph is described. The chronograph functions according to chromatographic principles to develop a perceptible visual image or pattern on an indicator panel or display area, which serves as a means to monitor the relative amount of time that elapses. The chronograph includes a self-contained reservoir for an activating agent, which once activated creates a mobile front that traverses the indicator panel substrate from the reservoir to a distal end at a predetermined rate. The chronograph may be used as a stand-alone device or may be incorporated as part of various articles or products, for instance, as either a training aid or as a dryness indicator. Methods for using and making the chronograph are also described.

32 Claims, 9 Drawing Sheets

U.S. PATENT DOCUMENTS

| | | | |
|---|---|---|---|
| 5,446,705 A | 8/1995 | Haas et al. | |
| 5,468,236 A | 11/1995 | Everhart et al. | |
| 5,469,145 A | 11/1995 | Johnson | |
| 5,518,927 A | 5/1996 | Malchesky et al. | |
| 5,602,804 A | 2/1997 | Haas | |
| 5,633,835 A | 5/1997 | Haas et al. | |
| 5,633,836 A | 5/1997 | Langer et al. | |
| 5,699,326 A | 12/1997 | Haas et al. | |
| 5,715,215 A | 2/1998 | Haas et al. | |
| 5,719,828 A | 2/1998 | Haas et al. | |
| 5,785,354 A | 7/1998 | Haas | |
| 5,796,345 A | 8/1998 | Leventis et al. | |
| 5,797,344 A * | 8/1998 | Ramsey et al. | 116/206 |
| 5,817,076 A | 10/1998 | Fard | |
| 5,822,280 A | 10/1998 | Haas | |
| 5,929,747 A * | 7/1999 | Rosenblatt et al. | 340/309.7 |
| 5,930,206 A | 7/1999 | Haas et al. | |
| 5,974,003 A | 10/1999 | Pedicano et al. | |
| 5,976,881 A | 11/1999 | Klingner | |
| 6,203,496 B1 | 3/2001 | Gael et al. | |
| 6,295,252 B1 | 9/2001 | Holt et al. | |
| 6,297,424 B1 | 10/2001 | Olson et al. | |
| 6,307,119 B1 | 10/2001 | Cammarota et al. | |
| 6,452,873 B1 | 9/2002 | Holt et al. | |
| 6,580,013 B1 * | 6/2003 | Belloso | 604/361 |
| 6,617,488 B1 | 9/2003 | Springer et al. | |
| 6,635,797 B2 * | 10/2003 | Olson et al. | 604/361 |
| 6,710,221 B1 | 3/2004 | Pierce et al. | |
| 6,752,430 B2 | 6/2004 | Holt et al. | |
| 6,790,670 B2 | 9/2004 | Munagavalasa et al. | |
| 6,796,065 B2 | 9/2004 | Haas | |
| 6,916,116 B2 * | 7/2005 | Diekmann et al. | 374/102 |
| 2003/0153891 A1 | 8/2003 | Molee | |
| 2004/0120904 A1 | 6/2004 | Lye et al. | |
| 2005/0124947 A1 | 6/2005 | Fernfors | |
| 2005/0130253 A1 | 6/2005 | Lye et al. | |
| 2005/0137542 A1 | 6/2005 | Underhill et al. | |
| 2005/0185520 A1 | 8/2005 | Haas et al. | |

FOREIGN PATENT DOCUMENTS

| | | |
|---|---|---|
| JP | 2002153503 | 5/2002 |
| WO | WO 01/82004 | 11/2001 |
| WO | WO 02/075441 | 9/2002 |
| WO | WO 03/007088 | 1/2003 |
| WO | WO 03/070138 | 8/2003 |
| WO | WO 2006/060060 | 6/2006 |

OTHER PUBLICATIONS

Ellison, S., "Un-Pampered: Tots Face Strict Deadline onToilet-Training," *The Wall Street Journal*, Aug. 27, 2004, 4 pages.

Pepe, R. C. et al., "Colorant Cross Index," *International Cosmetic Ingredient Dictionary and Handbook*, 9th Ed., vol. 4, Sect. 12, 2002, published by The Cosmetic, Toiletry, and Fragrance Association, ISBN: 1-882621-29-8 (4- volume set), pp. 3195-3199.

Spock, B., M.D., and Rothenberg, M.B., M.D., "Toileting-What Does It Mean?", *Dr. Spock's Baby and Child Care*, 6th Ed., 1992, ISBN: 0-671-75967-1, pp. 457-475

* cited by examiner

FIG. 5
A.
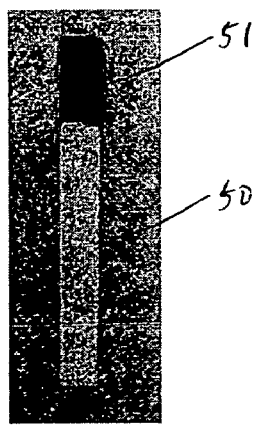
B.
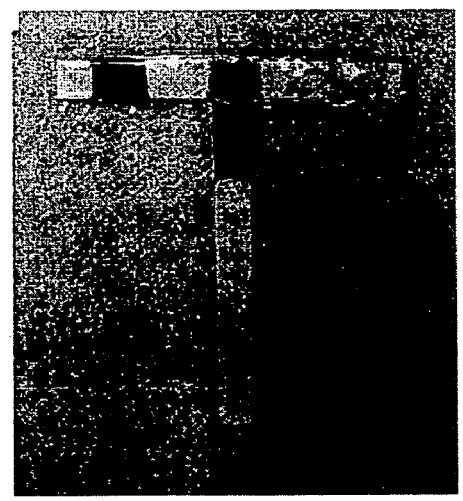
C.
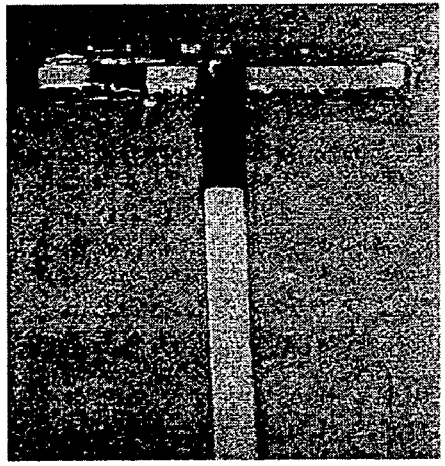
D.
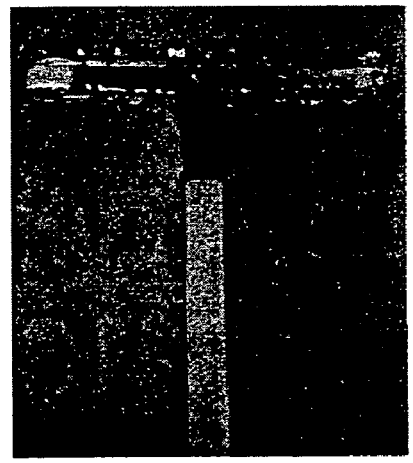

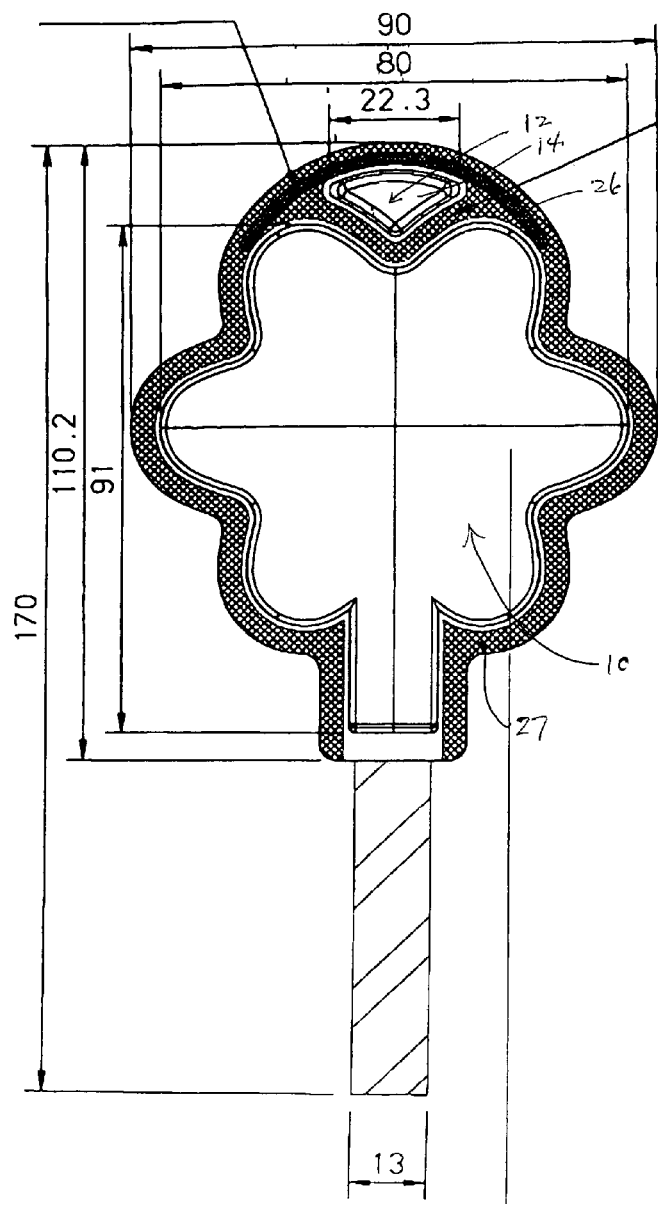
FIG. 6A
FIG. 6B
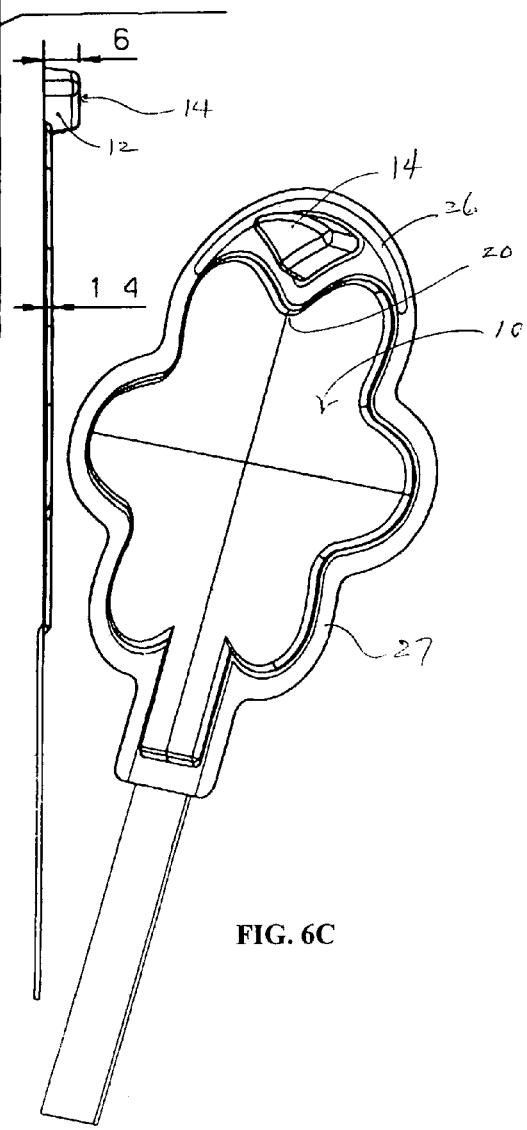
FIG. 6C

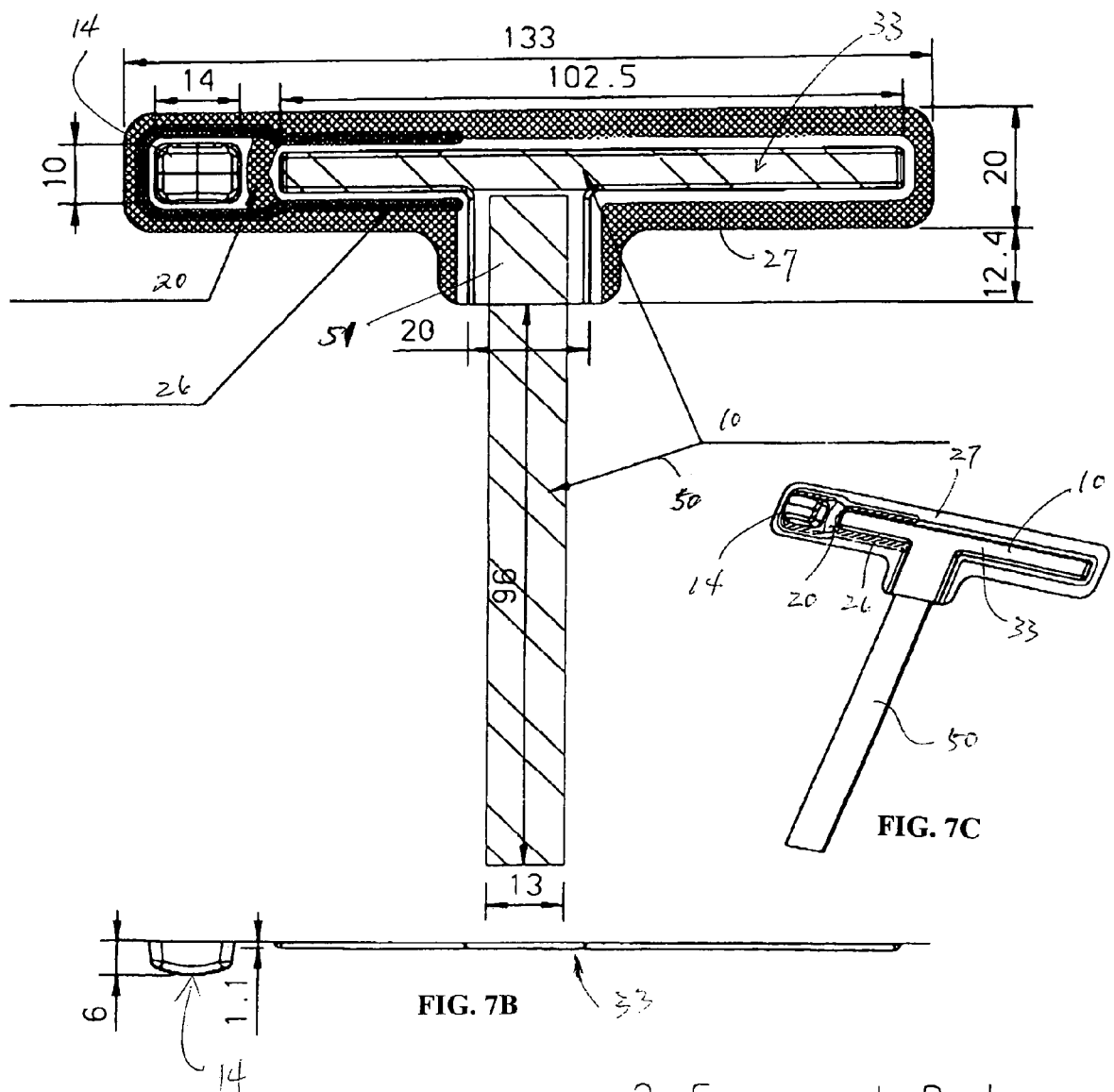

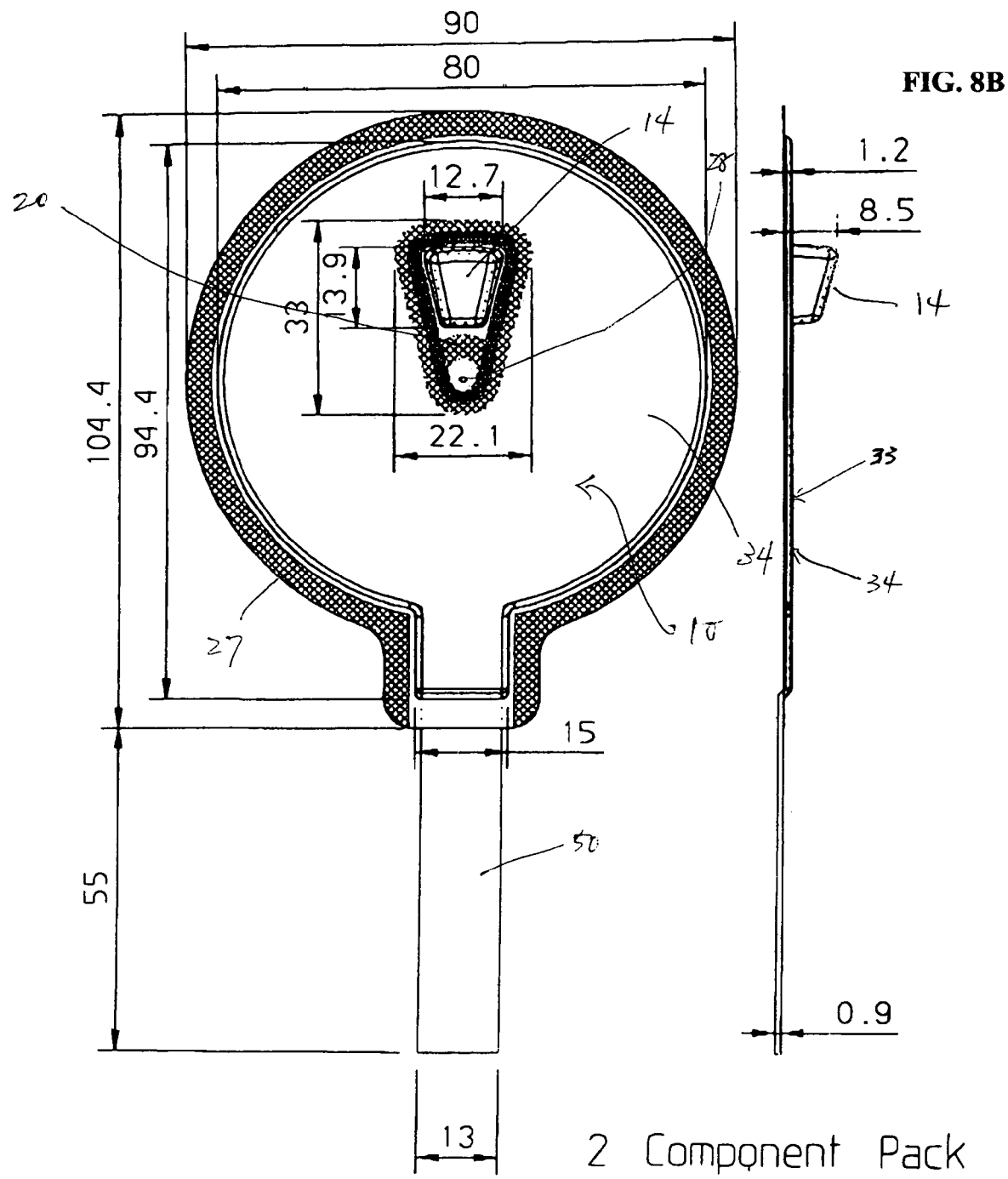

VISUAL INDICATOR CHRONOGRAPH AND THE USE OF THE SAME

FIELD OF INVENTION

The present invention relates to a device that incorporates a visually detectable indicator for monitoring the passage of time. More particularly, the invention describes a chronograph that uses visual cues and chromatographic development to mark the passage of time and to serve as a training tool.

BACKGROUND

In the realm of time monitoring devices and methods, one conventionally uses either a mechanical, electronic, or digital device which ticks off the seconds, minutes, and hours. To correctly use such devices or techniques, however, requires the user to have an understanding of the concept of time and to be able to interpret the meaning of abstract symbols. The ability to process the meaning of numbers on a digital clock or positions of clock hands, requires a relatively high level of cognitive functionality. To young children, for instance, who have yet to develop such a requisite level of cognitive function or an appreciation of the concept of time keeping, visual indicators of time are a better tool with which one can use to train and condition them. A visual indicator that changes its appearance gradually will allow the children to gain an appreciation for how time passes.

Examples of traditional techniques for measuring the passage of time by sight and the relative positions of markers have included the sun dial and the hour glass. The sun dial relies on the presence of the sun, a moving source of light, to cast a shadow. This feature, however, limits its applicability for nighttime or indoor uses. In the hour glass, sand gradually drains through from a full part of the glass to an empty part at a predetermined rate. Like the sundial, the hour glass also is limited as a training aid, because it can be easily reset and disrupted during the course of its run. A curtailed run of the hour glass does not help a child to fully develop the concept of time keeping and can have a negative impact on the conditioning or training processes. It is time, therefore, to update the concept of keeping time visually.

Numerous devices are known which provide a visual indication of the passage of a prearranged amount of time. Such time indicators are useful, for example when attached to perishables items for indicating the length of time the items have been on the wholesaler's or retailer's shelf. Thus, foods and other perishable items, such as photographic materials can be provided with indicators which evidence a visual change after activation and the passage of a predetermined period of time.

A need exists for a timer which is inexpensive and can clearly, relatively accurately and quickly indicate the passing of selected periods of time progressively, which can be adapted as a training tool. An ideal timer would be one where disruption is minimized and development can be tailored to almost any kind of application. The timer should also be easy to use and activated only when desired with a start mechanism, like in a stopwatch or chronometer. The visual timing mechanism should be simple and universal for all ages to use and understandable across all linguistic or cultural groups.

The present invention addresses the aforementioned need for a new type of visual time indicator that does not rely on external environmental conditions or stimuli for development, nor can it be disrupted inadvertently or without significant effort on the part of the user. The invention also lessens the need to have an initial appreciation of the concept of time, which makes it useful for young children or those with diminished mental capacities.

SUMMARY OF THE INVENTION

The present invention pertains, in part, to the development of a timing mechanism embodied in a device that is simple and can be appropriate for use by all age groups. According to one aspect of the invention, the device embodies a design concept adapted to reliably keep time. The device uses a visual indicator to signify the passage of time. In particular, the invention relates to an indicator that will show the relative amount of time that has elapsed from the initial activation of the indicator. The state of the indicator can be quickly and easily assessed by the progression of a visually perceptible change, either in color or design pattern, along different areas of the indicator. The device can be adapted to a host of potential uses which may have need of a timing element that can manifest on a display area for monitoring the relative progression of elapsed time.

In general, the device includes an indicator panel or display area on a substrate that is enclosed in an envelope or other packaging. As used herein, the term "indicator panel" or "indicator display" refers to any surface, shape or geometric configuration upon which a visual mechanism may be displayed or manifested such that one may observe the progress over time of either a colorant or mobile front. The display device may encompass a variety of surfaces or shapes. For instance, the basic indicator panel may be a flat, essentially two-dimensional surface. Alternatively, the indicator panel may have a three-dimensional curved surface, or be part of a shaped article or geometric form. The envelope is at least partially transparent to permit the user to observe the indicator area. On the indicator panel is situated either a design or some other visual configuration having a number of visually distinct sections or zones arrayed spatially relative to each other. The device further includes at least a self-contained reservoir that is in controlled communication with the indicator panel and the envelope enclosing the indicator panel. The system as a whole can be referred to as a chromatogram, since the indicator panel functions analogous to the absorbent column or strip of material containing the stratographically differentiated constituents separated from a solution of mixture by chromatography.

The reservoir contains an activating agent. The activating agent, once triggered or released from the reservoir interacts with the indicator panel. The activating agent generates a mobile front in or on the indicator panel, which passes along the indicator panel carrying along with it colorant from each of the visually distinct sections. Each of the visually distinct sections may be arrayed either adjacent to one another or spaced apart. Each section may be either monochromatic or multi-chromatic. Desirably, each section is monochromatic and of a different, contrasting color from its neighbor. Each visually distinct section may have colorant initially set up as a line or design pattern with a width that can expand and grow in area, even filling up the section and becoming more visually conspicuous, as the mobile front passes through.

As the mobile front progresses, it triggers the movement of the colorant from each section, which can be carried along either to the boundary of or into an adjacent section. The indicator panel in certain embodiments may be configured to either allow colorant from adjacent sections to bleed into or mix together. Alternatively, so-called "gates" in the indicator panel material can control either the rate or direction of elution of colorant from one section into another. The gates can be designed to stop one colorant or a set of colorants from traveling outside of its own section, hence color development may be confined within each section and not affect neighboring sections, even as the activating agent continues to travel through adjacent sections.

The indicator panel can take the form of either a substantially two-dimensional visual presentation or be part of a three-dimensional shaped surface or article. The display area of the chronograph can be of a size that ranges from an object that one is capable of holding within an average person's hand (e.g., linearly on the scale of about 2 or 3-12 inches or larger (about 4 or 5 cm to $\leq$20-30.5 cm)) to an object as large as a billboard (i.e., on the scale of one or two meters to several meters). The active portion of the indicator panel can be composed of materials selected from a group of cellulose or cellulose-polymer-based materials (e.g., a strip of wicking material), a gel, a plastic/polymer film, chromatographic separation materials, inorganic particles or oxides (e.g., $SiO_2$, $Al_2O_3$), or combinations of such materials. The reservoir may contain either a liquid or gaseous fluid. The liquid may be either water, a thixotropic material, an alcohol, or non-flammable solvent, or other organic species. For instance, the liquid can be a surfactant, a fatty acid, or an aliphatic alcohol. The gas may be either air, oxygen, carbon dioxide, a reducing gas, an inert gas (e.g., nitrogen, helium, argon), a moist gas (i.e., includes water vapor), or a mixture thereof.

A frangible seal is located between the reservoir and the indicator panel. When the frangible seal is ruptured, the timing element becomes activated, establishing communication between the reservoir contents and the indicator panel. Once activated, the activating agent enters or reacts with the indicator, proceeds along, either on a surface of or within the indicator panel at a predetermined rate. The rate at which the activating agent transgresses the indicator panel is likely to be expressed, for instance, on the order of either minutes, hours, or days, per unit of distance. The device may further include a negative feedback interference agent adapted to disrupt development of the timing element manifested on the face of the indicator panel. The negative feedback interference agent modifies the usual development and appearance of the indicator panel. Preferably, the indicator panel is finely tuned so as to graphically show when the interference occurred. In other words, at the time the negative interference is first introduced to the indicator panel, a mark, such as a chemical signature, or a point or line, will appear on the display, beyond which the activating agent development is either stopped or disrupted.

In another aspect, the present invention pertains to a method for providing a positive feedback to reinforce and condition an activity, the method comprises: providing a timed indicator device, such as described herein, activating the reservoir containing the activation agent, which forms a mobile front that travels across the panel at a controlled or predetermined rate, and conveying a feedback when the mobile front contacts or reacts with the display or indicator panel having a set of visually distinct or colored sections arrayed spatially relative to each other thereon. The visually distinct sections can either develop, such as to either change color or hue, or be carried along with the mobile front from one section to another.

Alternatively, the invention describes a method for providing a timer. The method includes providing a indicator comprising a design having a number of visually distinct sections arrayed spatially relative to each other on a display panel, and having at least a self-contained reservoir containing an activating agent; rupturing a frangible seal situated between said display panel and said reservoir to allow communication between said display panel and said reservoir; observing development of a mobile front across said display panel as the mobile front progresses from said reservoir to a distal end of said display panel over a predetermined time period.

Further, the indicator device can be used to as a timer for an activity or event that occurs progressively over time. For instance the device can be employed to monitor the duration for which an article or garment, such as a wound dressing or adult care products, has been applied or used. That is, a caregiver has the convenience to know at a quick glance of the visual indicator panel, for example, for how long an article has been on the patient, or whether the patient may require changing.

A method for using the timer may includes the steps of providing an indicator of the present invention, rupturing the frangible seal situated between the display panel and the reservoir to allow communication between the display panel and the reservoir, and observing development of a visually perceptible change over the display panel as the mobile front progresses from the reservoir to a distal end of the display panel over a predetermined time period.

The invention also provides a method for using the indicator to monitor duration of dryness. The method includes: providing a indicator, as described, having a set of colored zones arrayed spatially relative to each other, and having a self-contained reservoir for activating a timing element that manifests on an indicator panel; activating the timing element at a $T_0$; developing the timing element over a predetermined time period; and reading the indicator at a time $T_x$.

Additionally, we describe instructing how to use an indicator of the present invention to a user of an article that requires the monitoring for dryness. The instruction may include relating information about providing an indicator having a set of colored zones arrayed spatially relative to each other, and having a self-contained reservoir for activating a timing element that manifests on an indicator panel; activating said timing element at a $T_0$; developing the timing element over a predetermined time period; and reading said indicator at a time $T_x$. The instruction may further include relating about stopping the timing element development over the course of said predetermined time period by means of interaction with an insult or contact from an alternate moisture source.

Another application for the basic device can be as a training aid for conveying a positive feedback to reinforce maintenance of dryness in children's training pants. The indicator device on a training aid has a timing element which manifests itself on the indicator panel over a period of time in which the training aid remains active, through the development of the visual pattern or design over the course of the predetermined time period, hence providing a positive feedback signal. The positive feedback signal development is stopped when either the pattern on the indicator panel is interrupted or altered by the introduction of an alternate source of moisture or wetness, or when moisture is detected. The development of different colors, according to an embodiment, can appeal to children and enhance their willingness to use the training aid.

In another aspect, the invention relates to an assembly or kit having a chronograph with an indicator panel as described herein, and other component items that may have time-dependent or time-influenced functionality or use. The indicator can be either a stand alone article in the assembly or incorporated as part of a component of the kit assembly.

The invention also describes the use or incorporation of at least one indicator device for monitoring progression of time with any suitable personal care products, medical or surgical articles or garments. As used herein, the term "personal care product" refers to articles such as diapers, training pants, absorbent underpants, and adult incontinence products. Also, as used herein, the term "medical or surgical article or garment" refers to medically or therapeutically oriented items such as surgical gowns and drapes, face masks, head coverings like bouffant caps, surgical caps and hoods, examination and surgical gloves, footwear like shoe coverings, boot covers and slippers, wound dressings, bandages, sterilization wraps, wipers, garments like lab coats, coveralls, aprons and jackets, patient bedding, stretcher and bassinet sheets, and the like. Alternatively, the present timer device can be either used in conjunction with medical devices, such as disposable catheters, tubes, tracheal tubes which may require periodic maintenance, and the like.

The device includes a display having a number of visually distinct sections or zones arrayed spatially relative to each other, and having at least a reservoir for containing an activation agent, the activating agent that, when allowed to come into communication with the display, will interact with the display and the visually distinct sections to develop a timing element that manifests on said display over a predetermined time period. In certain embodiments, the article or absorbent garment can comprise at least an absorbent core and an outer sheet around the core. Alternatively, the absorbent garment may have a top sheet; a back sheet; and absorbent core disposed at least partially between the top sheet and back sheet.

In a further aspect, the invention relates to a method for providing a system for monitoring the duration of either insult-free wearing of a personal care article or use of an absorbent article. The method comprises: a) providing either a personal care article or an absorbent article incorporating a chronograph with an indicator display area having a number of visually distinct sections arrayed spatially relative to each other, and having at least a self-contained reservoir for containing an activation agent, said activation agent, when allowed to come into communication with said display area, interacts with said display area, traversing said display area developing over a predetermined time period at a predetermined rate; and b) providing instructions on how to use said chronograph to either a user or caregiver of either said personal care or said absorbent article, wherein said user or caregiver is enabled to determine relative duration of insult-free wear or use of said personal care article or said absorbent article.

Lastly, the invention relates a method of manufacturing the present chronographic device. The method includes the steps of: providing an indicator panel; placing the indicator panel in an at least partially transparent first enclosure; providing or forming a second enclosure; joining said first and second enclosures together as a housing unit with a frangible seal between said first and second enclosures. The method may further include sealing around an edge of each of said enclosures to create a hermetically sealed system. The reservoir can be joined to the first enclosure at a location proximal or adjacent to said indicator panel. The method can be repeated multiple times to fabricate as many of the housing units as one may desire. Individual housing units may be bundled or joined together to have a plurality of chromatographic timer indicators in parallel.

Additional features and advantages of the present time indicator device and associated articles of manufacture and methods will be disclosed in the following detailed description. It is understood that both the foregoing summary and the following detailed description and examples are merely representative of the invention, and are intended to provide an overview for understanding the invention as claimed.

BRIEF DESCRIPTION OF FIGURES

FIG. 4A shows the visual indicator strip at $T_0$, encased in the plastic sheath with a reservoir containing an activating agent at one end. After being activated and allowed to develop over an interval of time, FIGS. 4B and 4C show the same visual indicator strip at intermediate stages, $T_{0+n1}$ and $T_{0+n2}$, respectively. FIG. 4D is the same visual indicator strip as in FIG. 4A at $T_{xf}$ after complete development of the indicator.

FIG. 5 is a set of photos showing another embodiment of the present invention. FIG. 5A shows an interference or wetness indicator strip with a dark dye. FIG. 5B shows a timed visual indicator strip (horizontal) combined with the wetness indicator strip (vertical). FIG. 5C shows a timed visual indicator strip that has been activated by water and allowed to partially develop. FIG. 5D shows the same timed visual indicator strip as in FIG. 5C after the wetness indicator strip detects an alternate source of moisture (e.g., water or urine), which activates the dark color of the wetness indicator strip, and disrupts the development of the timing element on the timed visual indicator strip.

FIG. 6 shows an embodiment of the present invention according to the schematic of FIG. 2. FIG. 6A is a direct view, FIG. 6B is a side view, and FIG. 6C is a perspective view of the embodiment.

FIG. 7 shows an alternate embodiment of the present invention according to the schematic of FIG. 3. FIG. 7A is a direct view, FIG. 7B is a side view, and FIG. 7C is a perspective view.

FIG. 8 shows a alternative configuration of the embodiment of FIG. 7. FIG. 8A is a direct view, and FIG. 8B is a side view.

Figure 1:
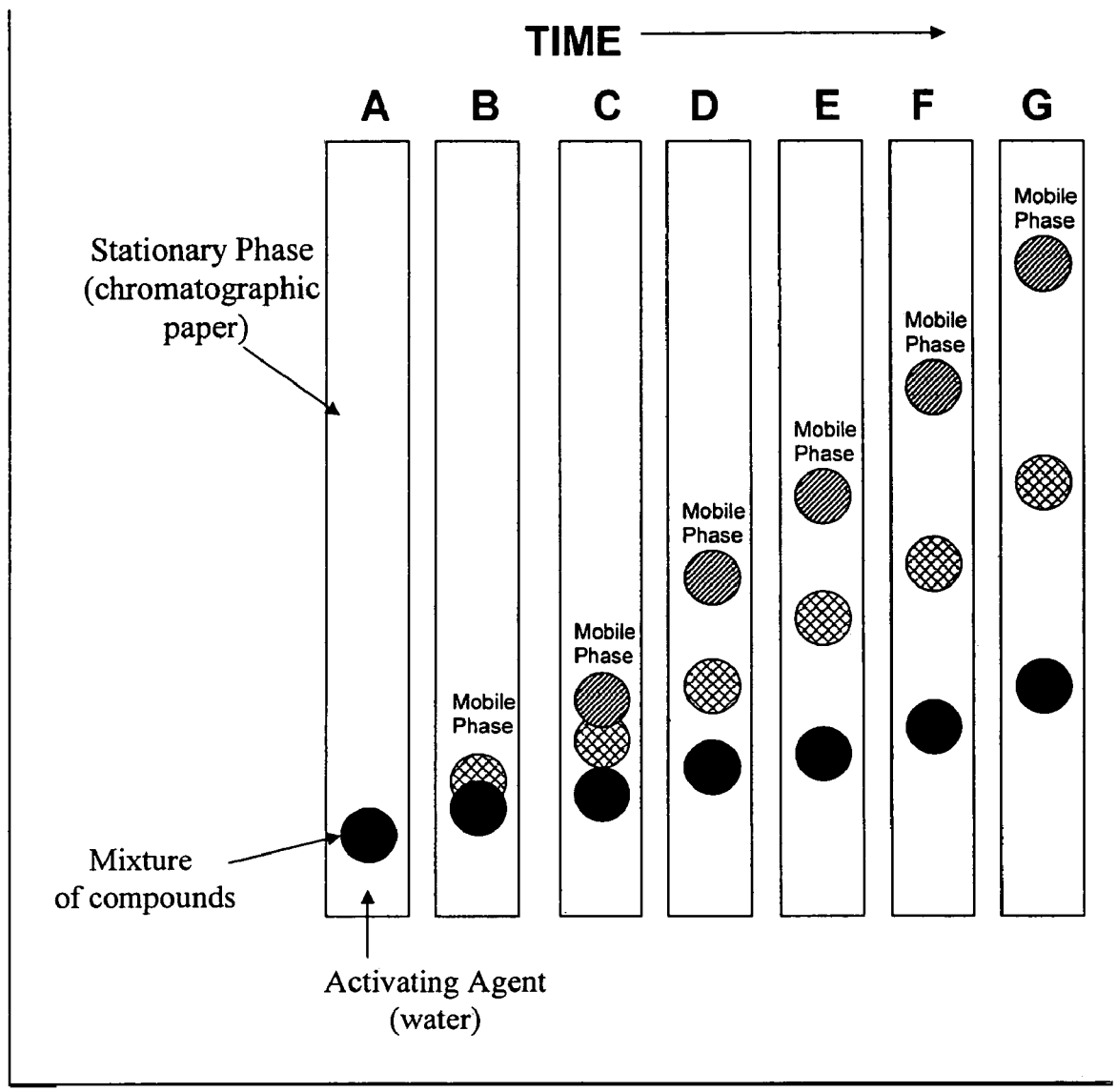
FIGS. 1A-1G is a series of schematic representations that illustrate the general concept of chromatography.

Repeat use of reference characters in the present specification and drawings is intended to represent the same or analogous features or elements of the invention.

DETAILED DESCRIPTION OF THE INVENTION

Before describing the present invention in detail, it is also to be understood that the terminology used herein is for the purpose of describing particular embodiments only, and is not intended to be limiting. All technical and scientific terms used herein have the usual meaning conventionally understood by persons skilled in the art to which this invention pertains, unless context defines otherwise. The present invention is not necessarily limited to specific compositions, materials, designs or equipment, as such may vary. As used in this specification and the appended claims, the singular forms "a," "an," and "the" include plural referents unless the context clearly dictates otherwise.

Section I.—General Function of Indicator Chronograph

The present invention relates to a time indicator device, or an instrument that registers and graphically records time intervals, such as the duration of an event. In particular, the invention describes a device that has an indicator panel or display area upon which the relative amount of time that has elapsed from the initial activation of the indicator can be rapidly and easily observed or determined by the progression of a mobile phase. The mobile phase or front creates a visually perceptible change either in color or design pattern along the indicator panel display. The visual indicator can be activated by the user at some time $T_0$ and develops over a predetermined time period to time $T_x$, hence providing a measure of the passage of time. It is envisioned that the device will be used for a variety of applications in which the relative passage of time is monitored, but knowing the actual time of day is not necessary. In other iterations, the invention includes associated articles of manufacture and methods for using the indicator and design concept.

Although devices or concepts that communicated the relative passage of time have been described, such as by Haas et al. in U.S. Pat. Nos. 5,058,088, 5,719,828, 5,785,354, 5,602,804, or 6,752,430, these prior devices function in a significantly different fashion than that of the present invention. Generally, the devices by Haas et al., for instance, utilize timing mechanisms that function by solid-solid diffusion; that is, diffusion of a solid dye into another solid state to produce a color change with time. Diffusion refers to the spreading out of a substance or entity from an area of high concentration to an area of lower concentration, which results in an increase in the entropy (degree of disorder) of the substance. As such, the prior work requires two solid substrates to activate their timer. A first substrate has a relatively low or no concentration of solid-phase dyes or inks, while the other, second substrate has a relatively high concentration of dyes. Hence, according to Le Chatelier's Principle, when the two substrates are placed in contact with each other, the first substrate functions as a sink into which the dyes of the second substrate diffuse gradually over time. An equilibrium is established between the two substrates as dye self-diffuses from one substrate into the other, unassisted by a fluid medium and driven by entropy, thereby producing a color change in the originally uncolored substrate.

In contrast, the present invention adapts the general principles of fluid chromatography for use in a graphical chronometer. Chromatography in the broadest sense refers to processes that permit the resolution of a mixture of components as a consequence of differences in the rates at which the individual components of that mixture migrate through what is referred to as a stationary phase or medium under the influence of a mobile phase. "Fluid" as used herein refers to either a liquid or gaseous medium that can flow or move in, on, or through a substrate or space either by capillary action, surface wetting, chemisorption, physical entrapment, wicking, elution, or diffusion. In conventional applications, chromatography is used to separate mixtures of chemicals into individual components. Once isolated, the components can be evaluated individually. In all chromatography, the sample mixture is introduced (injected) or combined with a mobile phase and the mobile phase carries a sample mixture, such as a colorant in the present invention, through the stationary phase. Separation is achieved based on the differences in specific interactions of the components with the given stationary and mobile phases; the interactions are unique to each component.

The present chromatography-based invention uses a mobile phase (e.g., liquid or gas, etc.) to elute colorants across or through a wicking device. The basic timer device comprises a single-layer material substrate that forms the active display area of the indicator panel. This substrate is encapsulated within an envelope which isolates the indicator panel from outside contamination or interference. The envelope has a clear, transparent polymer film on at least one major surface to permit a user to see the development of the indictor design. If the timer is to form part of a garment or personal care product, the clear and transparent surface of the envelope should be the external or outwardly facing surface. An opposing side of the envelope may be either also clear and transparent or opaque. When the timer device is used as a stand-alone article, separate from any other product, both sides of the envelope can be transparent. It is envisioned that either the indicator panel itself or the surface of the transparent side of the envelope enclosing the indicator panel will have a series of marks placed either serially or concentrically outward from the reservoir. While the timing element itself cannot be on the surface of the envelope, the marks to indicate how much time has elapsed can.

In the present device, an activating agent becomes the mobile phase, also referred to as a mobile phase front, once the activating agent is triggered from a reservoir and begins to interact with the stationary phase of the indicator panel. In one version of the visual indicator, time element development occurs when some species laid down on a stationary phase moves through the stationary phase when an appropriate mobile phase is present. In liquid chromatography (LC), the mobile phase is generally either an organic or inorganic solvent or mixtures of solvents, including water. In gas chromatography (GC), the mobile phase is usually an inert gas, such as helium. For either liquid or gaseous media, one may use a substrate having a plurality of different affinities or selectivities.

If the indicator panel is made up of multiple species, the stationary phase can selectively attract components, since each compound in the mixture interacts at a different rate, and those that interact more strongly will move the slowest across the indicator panel, while those that interact weakly will move along the indicator panel quickly. By changing characteristics of the mobile phase and the stationary phase, different mixtures of species can be induced to move at various rates along the indicator panel, thereby producing a tailorable time development, or visual separation of colorants. Further refinements to this separation process can be made by changing the temperature of the stationary phase or the pressure of the mobile phase. This particular indicator uses either color development or the decrease or absence of color over time as the visual cue to a user, since the progress of the development correlates with the extent of time that has elapsed.

FIGS. 1A-1G illustrates the general concept. In one example, dyes or other types of colorants can be separated by means of application of a technique known as paper chromatography. Paper chromatography is a method of separation in which a mobile phase passes through a filter paper material. The mixture, such as a line or spot of dye, is situated on the filter paper. When an end of the filter paper is exposed to an appropriate fluid mobile phase, such as a liquid solvent like water, capillary action causes the solvent to flow. FIG. 1A shows a material, such as an ink spot, made up of a combination of colorants spotted at one end of a stationary phase substrate. As the liquid moves through the filter paper, the dye molecules will move with the mobile front of the liquid if they are more strongly attracted to the liquid molecules than to the paper surface moieties, but will remain or lag behind if they are more strongly attracted to the paper than to the water, as depicted in FIGS. 1B-G. If two or more dyes have been mixed to form an ink, they may move at different rates on the paper as the water moves up the paper. The components that are more soluble in the mobile phase move at a faster rate than those that are more attracted to the paper. The result is the formation of moving bands of color.

FIGS. 1B-1G, show that after exposure to a solvent (i.e., mobile phase, such as water) through or over the stationary phase, the ink separates into its constituent colorant components. Each separated "spot" can be assigned a Retention Factor (RF) that is characteristic of the specific dye(s) associated with each respective colorant. The RF is a ratio of the distance the "spot" travels relative to the distance the mobile phase travels. The RF is calculated by dividing the "spot" distance by the mobile phase distance. This ratio should be a constant that is characteristic of the dye(s) in a particular spot under a particular set of experimental conditions (e.g., paper chromatogram substrate, water solvent, etc.).

Section II.—Indicator Display Appearance

Generally, as depicted in the accompanying FIGS. 2-9, the chronograph device has an indicator panel 10 for displaying the progress of an activating agent 12. Before use, the activating agent 12 is stored in a reservoir 14. It is envisioned that the activating agent 12 can be triggered by breaking a frangible seal 20 that is situated between the reservoir 14 and the indicator panel 10. The activating agent to move out from the reservoir 14 as a mobile phase front 16, across the indicator panel 10 to a distal location or terminus 15 away from the reservoir 14. On the indicator panel 10 are arranged a number of visually distinct sections or zones 18, each of which may or may not be marked. Each individual section can be likened to a miniature blank canvas or background 17, upon which one can generate a visually perceptible change in color or appearance as the mobile phase 16 comes into communication with each section 18 of the indicator panel 10. Typically, according to the present invention, manifestation of visual changes is through the use of colorants. A colorant 22 configured, for example, as either a fine line, a colored block, or pattern(s) of lines is present in each section 18. As in chromatography, the mobile phase 16 carries along or mixes together the colorant species to produce a visual display on the indicator panel 10. A plurality of colored sections 18 may be arranged together to create larger regions or areas that are located either adjacent to each other or spaced-apart from each other along the indicator panel 10.

Figure 2:
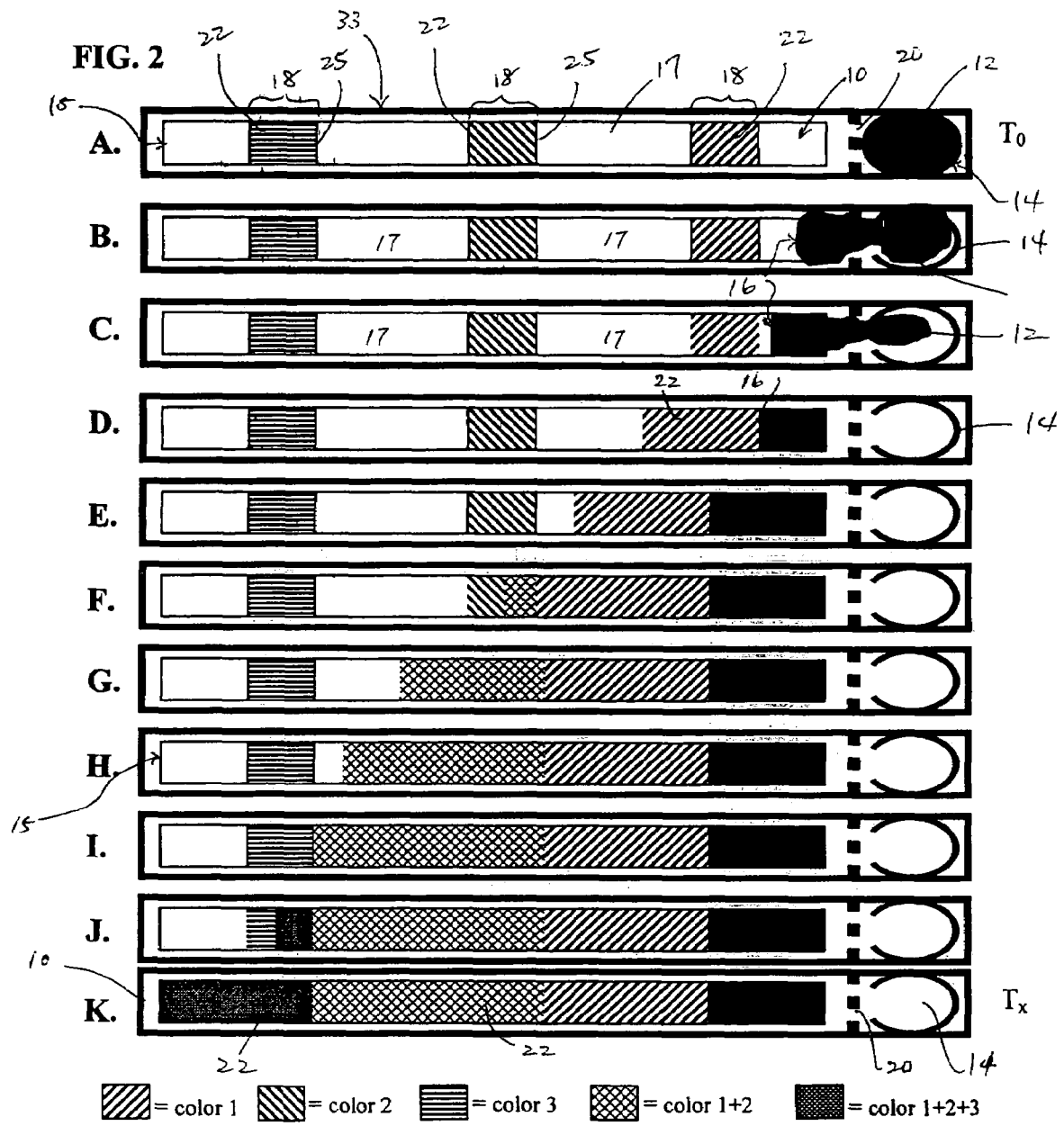
FIGS. 2A-2K depict a series of schematic representations of a basic iteration of a timed indicator according to the present invention, which adapts the principles of chromatography.

As time progresses, the mobile phase front 16 travels across the face 11 of the indicator panel 10, carrying with it individual colors 22 along from the respective sections 18 to create a spectrum across the indicator panel 10. FIGS. 2A-2K illustrate a series of schematic representations that show sequentially the progress of an activating agent 12 as it moves from a reservoir 14, right to left, across the surface of an indicator panel 10 from time $T_0$ (FIG. 2A) to a predetermined time $T_x$ (FIG. 2K). As the activating agent travels across the indicator panel, the mobile phase front 16 moves and carries molecules of the colorants 22 colorants through each section 18 and develops a visible perceptible image. It is envisioned that as the mobile phase as it moves forward passes through a number of sections 18, the mobile phase will cause changes and/or mixing of the colors of each section. In the embodiment shown in FIGS. 2 and 3, for example, the colorant 22 is located initially at one side or end of a section 18, with a neutral or white-colored background 17 either to one side of or surrounding the colorant. As the mobile phase front 16 passes through and first encounters the line of colorant, the colorant will be triggered and begin to tint or color the surrounding or adjacent background areas 17 of each section 18. Thus, the colorant 20 elutes throughout each of the visually distinct sections 18.

In chromatography applications, the stationary phase can be an absorbent column, sheet, or strip of material or filter of some sort. According to the present invention, other materials, as will be further discussed below, can be adapted to function in a similar manner. The stationary phase may take the form of a film or sheet, particle or other substantially two-dimensional or three-dimensional substrate bodies. The substrate can be packed with a number of stationary phases. Depending on the embodiment and particular conformations, the substrates can have a wide range of sizes and dimensions to accommodate the desired capacity or volume of the stationary phase, as people familiar with chromatographic techniques would understand. For instance, according to the present invention, the dimensions of a chromatographic column can be capillary in nature, desirably as small as microcapillaries on the order of about 0.01-0.05 micrometers (µm) or larger. Alternatively, the stationary phase may have columns on the order of about 0.5-20 µm, or more desirably about 1-10 µm. In extremely large cases, the column can be the size of tubing one may fine in petrochemical refineries, such as 1-5 meters in diameter, or silo tubes of about 10-50 meters across.

The stationary phase is usually contained in a form that isolates and protects it from the external surroundings, which may contaminate the stationary phase. The container should also prevent dilution, depletion, or escape of the mobile phase; as such, the mobile phase is maintained at a constant concentration and flow rate when interacting with the stationary phase of the indicator panel. Conventionally, containers can be made from glass or stainless steel of various dimensions. In the present invention, the indicator panel, likened to the stationary phase, also should be protected and enclosed in some form of envelope. The container for the indicator panel may be formed of either a tubular or flattened enclosure structure made from metal, glass, and suitable plastics.

According to an embodiment, the indicator display area may appear as a strip, such as shown in FIG. 2. When in the general configuration of a strip, belt, or other linear conformation, in which one dimension is significantly greater or longer than another, the sections may be arranged one next to another serially along a single row. According to one design, the indicator display area may be incorporated as part of a belt that wraps around a user's wrist or waist, or as part of suspenders or other article clipped to a garment. In such configurations, the reservoir can be located at one end of the device.

According to another design, the indicator may be in the form of a patch or other conformation having a wide and large surface area, such as in FIGS. 3 and 6-9. The indicator may have with a particular design, motif, or shape (e.g., circle, square, rectangle, triangle, polygon, sunburst, star, stripes, flower, animal, vegetable, or article (toy-shape or silhouette, hammer, wand, gun, sword, etc.)). When in the form of a patch, the indicator display area may be incorporated as part of the outer surface of a variety of products and articles, such as a garment, safety device, or absorbent article (e.g., diaper, inflatable float, pad). According to an embodiment, the reservoir can be located near a center of the surface area and the visually distinct sections may be arranged in a radial fashion, with rings or rows of sections radiating outward from the reservoir. Similar to FIGS. 2A-K, FIGS. 3A-3H show sequentially over time the outward, radial progress of an activating agent 12 from a reservoir 14 situated at the center of a circular design. As the activating agent travels through each of the colored sections 18, it changes the initial color of each zone or mixes the colors together.

In an alternative design, more than one row of visually distinct sections can be arranged parallel to each other over the surface of a single indicator panel with relatively large surface area or a corresponding number of parallel indicator panels. Each of the parallel indicator panels may be isolated in its own housing unit or the indicator panels can be in cross communication. The specific configuration and alternative designs will depend on the particular or desired use. When more than a single reservoir is included, one can have the potential for a combination of indicator display areas in parallel, or intersecting cross channels, which may allow two mobile phases to interact with and/or disrupt one other as they cross paths. Each individual reservoir can contain a different activating agent as the respective mobile phase, each of which has a different rate of progression along the respective stationary phases.

The colorant used to distinguish each visual distinct section or zone may be a different dye, pigment, or tint, or the absence of pigment color, such as black/white. Alternatively, each of the visually distinct sections of the indicator display panel can have the same colorant. For instance, one may have a sealed wicking strip that has situated on the strip areas (e.g., spots or stripes) of food, drug and cosmetic (FD&C) dyes which render certain parts or zones of the indicator a specific color. Each zone can have a different color from the zone adjacent, hence providing a simple color-coded visual feedback. In such a situation, each section will have an initial background that is of a contrasting appearance or coloration to the subsequently developed coloration, when the colorant passes through with the mobile front. For example, the overall background of the indicator panel may initially look neutral or white, with either a single or plurality of fine colored lines (e.g., red, yellow, green, blue, or black) drawn within each section. After the activating agent is released from the reservoir, it travels as a mobile phase front either along or through the indicator panel, interacting with each of the colorants in turn. The mobile phase front typically carries the colorant along, turning the once neutral background the color of the colored lines. Thus, with the change in color or appearance of the indicator panel, one may clearly observe the progress of the mobile phase front as it passes along at a predetermined rate. In such a situation, the colored lines or patterns are arranged in series, one for each visual section. Preferably, the line or pattern may be either of the same or different color. According to some embodiments, visual color change may result from a blending or mixing of different colorants preexisting on the indicator panel, such as shown schematically in FIGS. 2 and 3. For examples, a green color can be created when a yellow colorant carried by the mobile phase mixes with a blue colorant. In certain other embodiments, the visual manifestation of colors could be caused by reaction between one or more materials of the indicator area and the activating agent material as it progresses along. For example, a yellow mobile phase moves into a blue line generates green.

Figure 3:
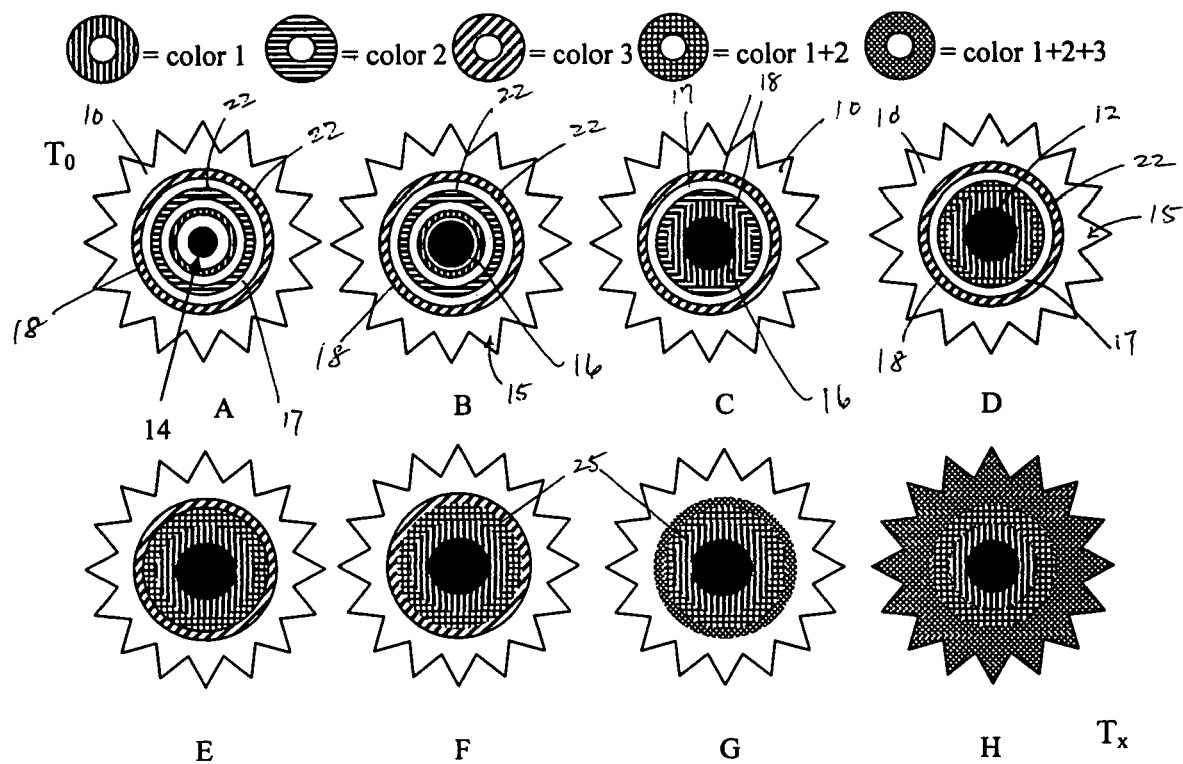
FIGS. 3A-3H depict a series of a schematic representations of an alternate design for the indicator of the present invention.

According to certain embodiments, across the indicator display area may be located a series of ionic gates 25, such as depicted in FIGS. 2 and 3, either on or in the surface of the indicator panel. The ionic gate can be created by applying a charged polymer molecule to a part of the indicator panel in the pathway of the mobile phase front. To illustrate, once the activating agent moves through one section, it carries along a colorant, such as a dye, until the mobile phase front reaches the next ionic gate. Salt concentration may halt the ionic diffusion of charged colorants while permitting the activating agent to continue through. In some embodiments, according to this fashion, one produces zone of charged polymer molecules.

The ionic gates can function first as time markers, and to control the direction of elution. That is, the ionic gates can prevent the backward flow of disruptive dyes or other indicators, which can interrupt forward progress of the activating agent, and can destroy a visual marking of how far the activating agent has progressed over a certain time. Each ionic gate can be spaced apart a known given distance. Since the rate at which the activating agent travels along the indicator panel is known, by the elution rate of the colorant molecules, one can easily calculate the time interval elapsed as the activating agent traverses the distance between two adjacent ionic gates. As FIGS. 2-9 show, depending on the particular design or configuration of the indicator panel, the ionic gates can be arranged either in a lineal fashion to form part of a strip, or in concentric rings to form part of a larger circular or elliptical design.

Once the activating agent is released from the reservoir, the agent will elute across the indicator panel, either within a sheet or other wicking medium, as in some embodiments, or along one or more specially designed channels, as in other embodiments. The distance and time for a particular activating agent to travel through the indicator panel will be predetermined and can be calibrated to certain durations. As illustrated herein, the surface of either the indicator panel itself or an outer covering of an enclosure to protect the indicator can be marked-off with a number of lines for each color development zone. The lines may represent increments of time. For instance one centimeter or inch can represent a duration of either as short as a few minutes, (e.g., 5-30 min.) up to about an hour or two, or as long as a week to a month. Typically, it is envisioned that the markings on the chronograph will represent time increment of a few hours to a few days. An activating agent that elutes relatively swiftly for short running times, for instance, can have a rate such as 0.01 or 0.1 mm/second, or 1 inch/minute, which permits the chronograph to operate for either a few minutes or a few hours, up to a day. Alternatively, one may select an activating agent that elutes slower for operations that have need for longer running times. Desirably, the development of the visual display on the indicator or chromatogram still should be at a rate that will permit the chronograph to be visually perceptible and able to operate over prolonged periods, such as several days, weeks, months, or possibly even years. For example, the mobile phase may progress at as slow a rate as $1\times10^{-7}$ mm/second, or $1\times10^{-9}$ inch/minute. Of course, in the creation of chronograph devices for either short or prolonged durations, one should consider and balance several parameters, such as the rate of elution and the physical dimensions or size of the display panel, to produce an optimized design.

Figure 4:
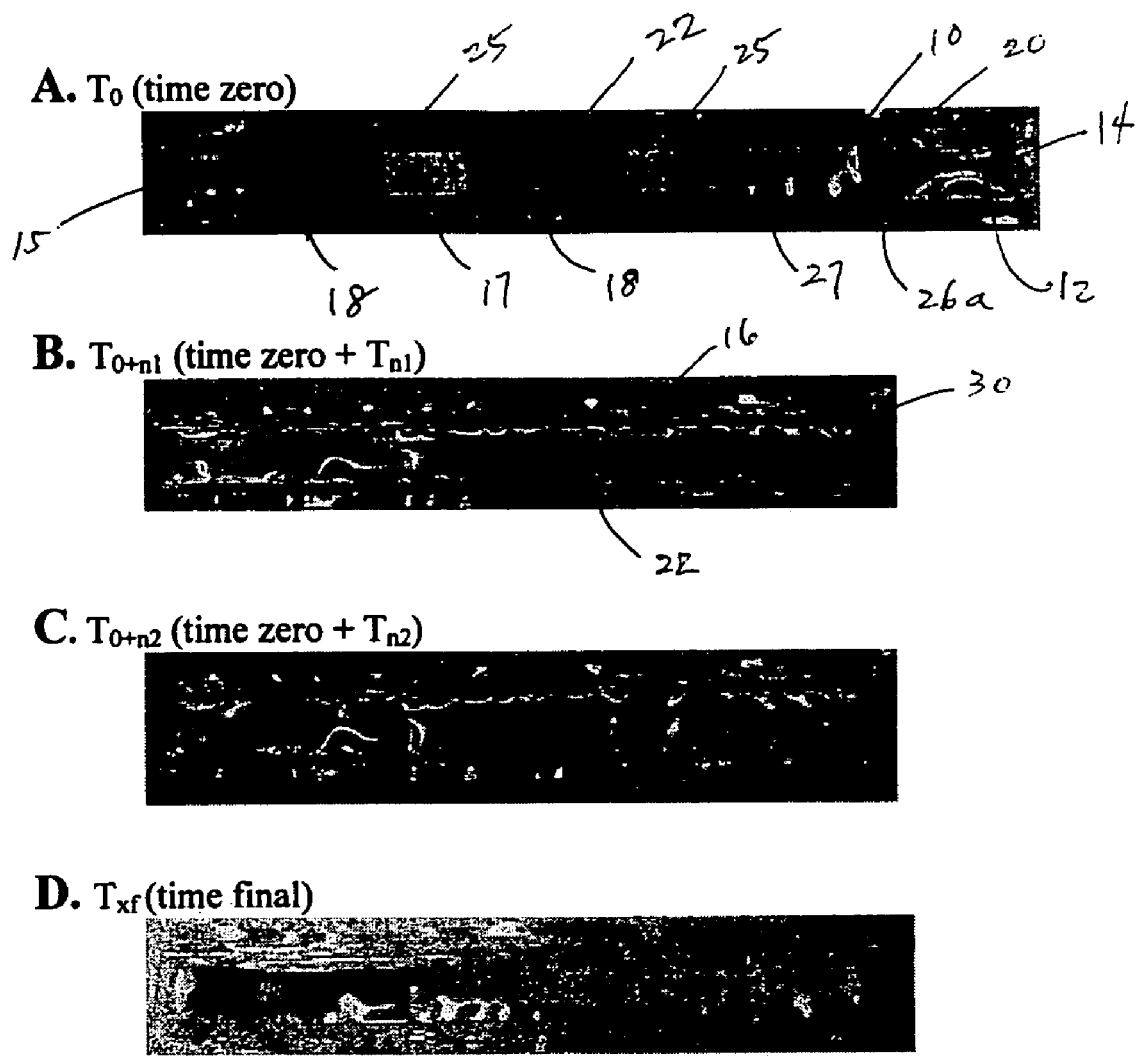
FIG. 4 is a set of photos showing an embodiment of the present invention having a visual indicator strip made from a wicking material enclosed in a plastic sleeve.

The concept illustrated in FIG. 2 and expanded to include alternate designs in FIG. 3, is demonstrated in FIGS. 4A-D. According to an embodiment, timed visual indicator strips are created using wicking materials and FD&C approved dyes (yellow 5, red 4 and blue 1). The wicking strips are cut into a desired length (~4-4.5 inches) and the desired width (~0.5-1 inch). The dye solutions (50 mg in 10 ml of water; 0.5 wt %) were located on the wicking material (0.02-0.04 ml) at predetermined interval distances, after which the strip was encased in a plastic coat and the plastic coat was heat sealed. In the example shown in FIG. 4, a small amount of water (~0.2 ml) is introduced to the timed indicator strip and allowed to develop over a predetermined time interval. The desired time to complete the elution from one end of the strip to the other, right to left, was about 2-3 hours. The duration of development time can be a function of the volume of water added. FIG. 4A shows the initial condition at $T_0$. FIGS. 4B and 4C show intermediate stages of development, at about 10 minutes ($T_{0+n1}$) and about 40 minutes ($T_{0+n2}$), respectively. FIG. 4D shows the indicator after about 140 minutes ($T_{xf}$).

Section III.—Indicator Material Components

A variety of potential materials and techniques may be employed to create the time indicator device. According to an embodiment, one may use a wicking material for the body of the indicator panel. The particular type of wicking material can include, for example, cellulose based materials having a basis weight range of about 10 to about 400 or 500 grams per square meter (gsm). More typically, the wicking material can have a basis weight of about 50-300 gsm, and desirably about 100-200 or 250 gsm. Other possible wicking material components may be composed of a cellulose/polyolefin material combination, having for instance a basis weight in the range of about 10-475 gsm. Still other materials may include polymeric, polyolefin-based, and other suitable synthetic materials.

Examples of particular materials may include wire texture coform laminates (WTCL), wet-laid, bonded-carded web, or combined fibers. (Commercial examples of such materials include products by Kimberly-Clark Corporation such as WypAll™X80, Viva® scrub cloth, Hydroknit®, Spunlace®, or Ironman™ airlaid materials.) Still another wicking material can be selected from the universe of non-woven materials (e.g., spunbond, meltblown, melt-spun, or spunbond-meltblown-spunbond (SMS) laminates). Non-woven materials may also include polyolefins (e.g., polylypropylene or polyethylene). Examples of suitable polymeric materials can include a sheet or substrate composed at least in part of fibrillated polyethelene, Hydroknit® with polypropylene fibers, fuzzy foam or bonded carded webs.

Alternatively, chromatographic materials, such as inorganic and/or organic particles or oxides can be incorporated into the indicator display panel. These materials should be inert and have an affinity for either the colorant in each of the sections of the indicator panel and/or mobile phase (activating agent). The inorganic components, for instance, may include silica, alumina, titania, clays, powdered zeolite, or kieselgur powder (porous diatomite) and could be used as part of the indicator panel. The inorganic species can be modified with either acidic or alkaline functionality, so as to create additional affinity for or repulsion of colorants carried in the mobile phase. Organic components may include carbon, starches (e.g., dextrose), cellulosic materials (e.g., paper), or plastic and polymers such as polystyrene, polyolefins (e.g., polybutylene, polyethylene), polyesters (e.g., polyethyleneterephthalate), polyamides (e.g., nylon), or poly(hydroxyl methacrylates).

The indicator display panel should be enclosed to contain the activating agent while the agent reacts with the panel. The containment envelop should be large enough to easily allow the user or caregiver to view the indicator panel enclosed within, and may be made from a film that is transparent either on both sides of the envelope, or transparent along at least one major side while being opaque on the opposing side. Suitable material examples for making such films may include polyolefins, polyesters (e.g., PET), polyamides (e.g., nylon), silicones, or inorganics (e.g., mica (as a backing), metal, ceramics, glass-ceramics, or glass).

In an alternative approach, the present visual indicator can also develop based on the principles of oxidation/reduction, whereby exposure to the activating agent causes a color change, or removal of color, in the surrounding environment of the indicator panel with increasing exposure times, again providing the user with a visual cue as to the extent of time elapsed. Examples include oxidation or reduction of metallic salts of transition metal ions (e.g., Cu, Co, Cr, Fe, Mn, Ni, Ti, V, or Zn), or a moisture absorbent calcium carbonate compound (e.g., Drierite® from the W.A. Hammond Company, Xenia, Ohio) coated with a dye that turns from blue to pink the longer the compound is exposed to a source of moisture. Alternatively, the calcium chloride layer can be coated on the inner surface of channels or interstices, as between two film layers, to serve as a counter indicator. When an activating agent makes contact with the calcium chloride, it will turn from blue to pink on the indictor panel.

The colorant materials located within the visually distinct zones of the indicator panel can include or be selected from potentially hundreds of different dyes, inks, colored particles, microencapsulated colors, or pigmentation compounds. These kinds of materials may be further divided into generally hydrophilic or hydrophobic species. (See for example, Ranae Canterbery Page, John A. Wenninger, Gerald N. McEwen, Jr., Ph.D., J. D., Ed., INTERNATIONAL COSMETIC INGREDIENT DICTIONARY AND HANDBOOK, 9th Ed., Vol. 4, Sect. 12, "Colorant Cross Index," pp. 3195-3200, ISBN: 1-882621-29-8 (4 volume set), The Cosmetic, Toiletry, and Fragrance Association, Washington, D.C. (2002)). Hydrophilic colorants can include water soluble or miscible dyes or pigments, dyes that contain sulfonic or carboxylic acids or acid salts, or hydroxyl moieties. Examples of these are acid dyes, basic dyes, azo dyes, natural dyes, fast dyes, brilliant dyes, Food Drug & Cosmetic (FD&C) dyes, or Drug & Cosmetic (D&C) dyes. Hydrophobic colorants can include oil or other organic soluble or miscible materials, such as dyes lacking sulfonic or carboxylic acid/salt moieties; for instance, direct dyes, mordant dyes, dispersed dyes, pigment dyes, solvent dyes, and oil-based dyes. Desirably, the colorants and/or activating agent are harmless food or cosmetic dyes and pigments suitable for contact with bare human skin, or other types of dyes as contemplated.

In an alternative example for development of color, the strip has no lines of color, rather a single line or spot of black/brown. When the mobile phase front hits the spot or line it carries the multicolor containing spot. Each color contained in this mixture will wick at a different rate across the wicking strip, generating a vivid color spectrum or rainbow of colors as the mobile phase migrates across the strip. This separation of colors follows simple paper chromatography principles where each color has a different solubility in the mobile phase and different hydrophilic/hydrophobic (HL/HB) mixes which make the colors move at a different rate as compared to other colors of different HL/HB mix. The resultant effect of this novel blend is to generate a visual attractive/appealing spectrum of colors from a dull spot or line at one end of the strip.

In another embodiment or variation for generating color for the visual indicator, color-changing, solvent-sensitive, solvatochromic dyes can be immobilized in or on the stationary phase to create a visual indicator panel substrate or strip. Solvatochromic dyes change color when the environment in which they reside changes, typically according to the polarity of the fluid, usually a liquid, in which they are dissolved. They have been proposed as indicators of solvent composition, but in order to make a practical sensor such a dye must be immobilized in such a way as to retain solvatochromic behavior, and its color measured in a reliable manner. For example, an environmental change occurs when solvatochromic dyes interact with the mobile phase. As the mobile phase moves past the solvent sensitive dyes, it causes a change in the color of the dye. There are a variety of dyes, each of a unique and different color. Hence, as the mobile phase front comes in contact with the dye or mixture of dyes in each zone, the color change generates a visually attractive and appealing indicator panel. Examples of solvatochromatic dyes may include, for instance: Reichardt's dye (Aldrich Chemical Co., Milwaukee, Wis.), or 1-Docosyl-4-(4-hydroxystyryl)-pyridinium bromide (Aldrich Chem Co. Inc., Milwaukee Wis.). Reichardt's dye is a phenolbetaine, which shows very strong negative solvatochromism, and is of the structure (R1-R5=phenyl):

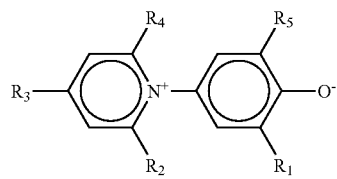

Solvatochromic dyes of this class have been synthesized, covalently immobilized onto silica or polystyrene, and changes in color in response to changes in solvent or to impurities in solvent have been measured. Immobilization on the substrate can be achieved through a link from the 4 position of R3 to the solid support, and the spectral response of the dye has been modified by varying the substituents $R_1$, $R_2$, $R_3$, and $R_4$.

Listed in Table 1 are a few examples of the general classes of compounds we believe to be good colorants in each of the section on the indicator display area. These examples of possible compounds are by way of illustration only, and they are not exhaustive, nor should they be construed to be limiting. Other suitable compounds may be readily determined by one skilled in the art.

TABLE 1

A. Structures of FD&C Blue 1 (top left), FD&C Red 4 (top right) and FD&C Yellow 5 (bottom).

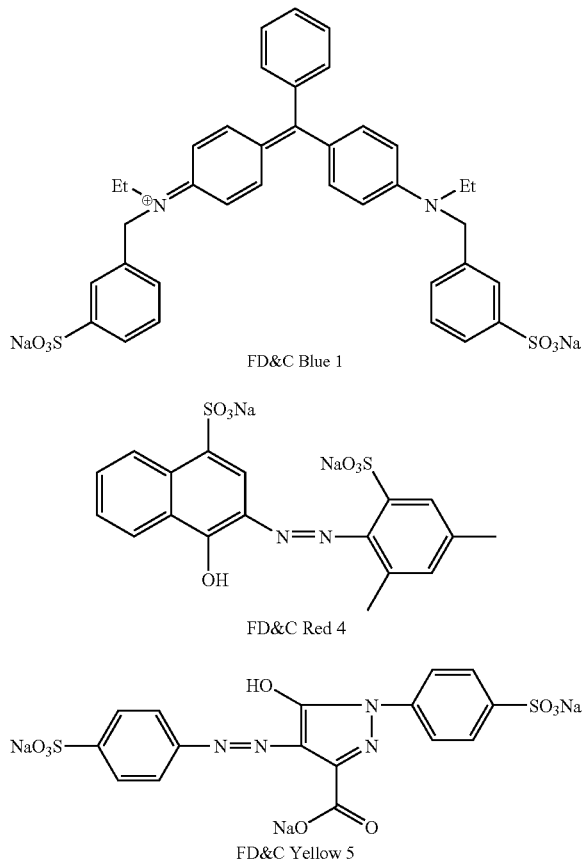

B. Dyes containing the Anthraquinone (5) Chromophore:

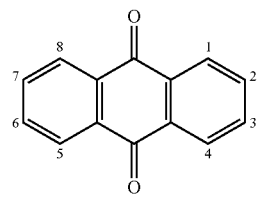

Numbers indicate the substitution positions of the anthraquinone structure. The following sections of the table indicates dye substituents that occur at positions 1, 4, 5, or 8 on the anthraquinone structure. In other words, this table shows the presence of groups that form alumina bonding moieties 1 through 5.

| Name | Substituent at position 1 or 4 or 5 or 8 | Other groups present include |
|---|---|---|
| CI Acid Black 48 | $NH_2$ | $SO_3Na$ |
| CI Acid Blue 25 | $NH_2$ | $SO_3Na$ |
| CI Acid Blue 40 | $NH_2$ | $SO_3Na$ |
| CI Acid Blue 41 | $NH_2$ | $SO_3Na$ |
| CI Acid Blue 45 | OH, $NH_2$ | $SO_3Na$ |
| CI Acid Blue 129 | $NH_2$ | $SO_3Na$ |
| CI Acid Green 25 | NHAr | $SO_3Na$ |
| CI Acid Green 27 | NHAr | $SO_2Na$ |
| CI Acid Green 41 | OH, NHAr | $SO_3Na$ |
| CI Mordant Red 11 (Alizarin) | OH | |

TABLE 1-continued

| Colorant | Substantive Group | Chromophore |
|---|---|---|
| CI Mordant Black 13 (Alizarin Blue Black B) | OH, NHAr | SO₃Na |
| Alizarin Complexone (Aldrich 12, 765-5) | OH | |
| CI Mordant Red 3 (Alizarin Red S) | OH | SO₃Na |
| CI Natural Red 4 (Carminic Acid) | OH | COOH |
| CI Disperse Blue 1 | NH₂ | |
| CI Disperse Blue 3 | NH(alkyl) | |
| CI Disperse Blue 14 | NHCH₃ | |
| Emodin (6-methyl-1,3,8-tri-hydroxy-anthra-quinone) | OH | |
| Nuclear Fast Red (Heliofast Rubine BBL) | OH, NH₂ | SO₃Na |
| CI Natural Red 16 (Purpurin) | OH | |
| CI Natural Red 8 | OH | |
| Quinalizarin | OH | |
| Quinizarin | OH | |
| CI Reactive Blue 2 | NH₂, NHAr | SO₃Na |
| Solvent Green 3 | NHAr | |

C. Dyes Containing Salicylate, or 3-hydroxy-2-naphthoic acid moieties:

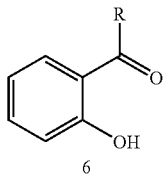 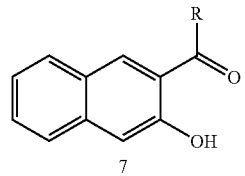

6  7

Dyes containing salicylate (6, R=OH), Salicamide (6, R=NH₂, NHAr, NHAlk), or BON acid (3-hydroxy-2-naphthoic acid) (7, R=OH) or a nitrogenous BON acid derivative (7, R=NH₂, NHAr, NHAlk), moiety as shown below may also be used in accordance with the present invention. These dyes often fall into the Color Index Mordant application class.

| Colorant | Substantive Group | Chromophore |
|---|---|---|
| Aluminon (tri ammonium salt) (Aurintricarboxylic acid) (CI Mordant Violet 39 is the trisodium salt) | Salicylate | TPM |
| CI Mordant Blue 29 | Salicylate | TPM |
| CI Mordant Blue 3 (Chromoxane Cyanine R) | Salicylate | TPM |
| Calconcarboxylic acid 3-hydroxy-4-(2-hydroxy-4-sulfo-1-naphthylazo)-2-naphthalenecarboxylic acid | BON acid | Azo |
| CI Mordant Orange 1 (Alizarin Yellow R) | Salicylate | Azo |
| CI Mordant Orange 6 (Chrome Orange GR) | Salicylate | Azo |
| CI Mordant Orange 10 | Salicylate | Azo |
| CI Mordant Yellow 7 | Salicylate | Azo |
| CI Mordant Yellow 10 | Salicylate | Azo |
| CI Mordant Yellow 12 | Salicylate | Azo |
| CI Mordant Green 31 (Naphtho Chrome Green) | BON Acid | Azo |
| CI Azoic Coupling Component 2 (Naphthol AS) Arylamido | BON acid | N/A |
| CI Azoic Coupling Component 45 (Naphthol AS B1) Arylamido | BON acid | N/A |
| 3-hydroxy-2-naphthoic acid (BON acid) | BON acid | N/A |
| Xylidyl Blue 1 Aryl amido | BON acid | Azo |

D. Dyes based on Chromotropic acid:

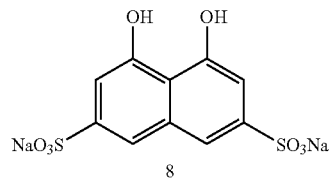

8

Dyes based upon Chromotropic acid (8) are also substantive to alumina. Azo dyes are formed when chromotropic acid is reacted with a diazonium salt. Azo coupling occurs at positions 2 and/or 7.

Colorant

CI Acid Red 176 (Chromotrope 2B)
CI Acid Red 29 (Chromotrope 2R)
Plasmocorinth B
Sulfonazo III
(3,6-Bis(2-sulfophenylazo)-4,5-dihydroxy-2,7-naphthalene disulfonic acid sodium salt) 2-(4-sulfophenylazo)-1,8-dihydroxy-3,6-naphthalenedisulfonic acid E. Naphthoquinone Colorants:

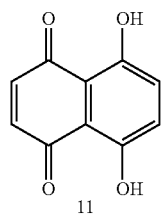

11

Naphthoquinone (11) type structures are also useful for forming complexes with the surface of alumina. CI Natural Black 1 (Hematoxylin) is another example of a dye that contains quinoid groups and is substantive to alumina.

F. Aluminum Dyes; Dyes Known to be Useful for Staining Anodized Aluminum.

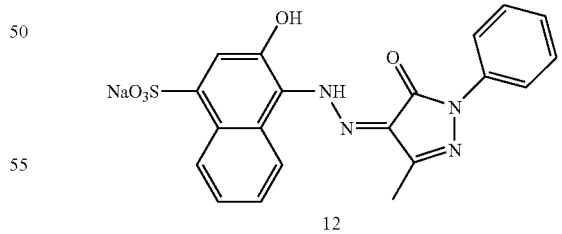

12

There are several dyes that are know to be useful for the coloration of anodized aluminum, including CI Mordant Red 7 (Eriochrome Red B), (12). It is believed that the geometry of the five membered pyrazolone ring oxygen atom brings it into the correct position with the beta-naphthol group for complexation with alumina. Thus, the following structure can be considered a functional equivalent to a carbonyl-hydroxy moiety. The structure also contains an iminalogous amide moiety, which is functionally equivalent to a vinalogous amide.

TABLE 1-continued

G. Aluminum Lake Forming Dyes:
Certain anionic dyes may be precipitated using certain metal ions to form insoluble colored compounds know as Lake Pigments. For example, Erythrosine (Tetraiodofluorescein) forms an insoluble salt with aluminum ions. The salt is known as CI Pigment Red 172. CI Pigment Blue 36 is the aluminum lake of indigo disulfonate (FD+C Blue 1):

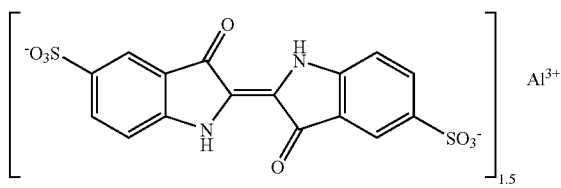

Various co-solvents may also be included in the ink formulation. Examples of such co-solvents include a lactam such as N-methyl pyrrolidone. However, other examples of optional co-solvents include N-methylacetamide, N-methylmorpholine-N-oxide, N,N-dimethylacetamide, N-methyl formamide, propyleneglycol-monomethylether, tetramethylene sulfone, and tripropylene-glycolmonomethylether. Still other solvents which may be used include propylene glycol and triethanolamine (TEA). If an acetamide-based cosolvent is also included in the formulation it is typically present at about 5 percent by weight, within a range of between about 1.0-12 percent by weight.
Optionally, one or more humectants in an amount between about 0.5 and 20 percent by weight may be included in the ink formula. Additional humectants for optional use in the formulation include, but are not limited to, ethylene glycol, diethylene glycol, glycerine, and polyethylene glycol 200, 400, and 600, propane 1,3-diol, other glycols, a propyleneglycolmonomethyl ether, such as Dowanol PM (Gallade Chemical Inc., Santa Ana, CA), polyhydric alcohols, or combinations thereof.
(See for example U.S. Patent Publication No. 20040120904)

The colorant compositions of the present invention may be applied to any substrate to impart a color to the substrate. The substrate to which the composition is applied may include, but is not limited to, paper, wood, a wood product or composite, woven fabrics, non-woven fabrics, textiles, films, plastics, and the like. In one aspect, the colorant composition or medium may be applied to textile articles, such as cloth.

Examples of some common solvents that may be employed in the present invention as an activating agent and mobile phase include: water, aqueous detergent solutions; acidic water solutions; alkaline water solutions; isopropanol; ethanol, methyl-ethyl ketone; acetone; toluene; hexane, ethyl acetate; or acetic acid (vinegar). Particular examples of an organic mobile phase to carry the colorants can include: cetyl alcohol (fatty alcohol), which can keep oil and water from separating; dimethicone silicone; isopropyl lanolate, myristate, and palmitate, lanolin and lanolin alcohols and oil; octyl dodecanol; oleic acid (olive oil); panthenol (vitamin B-complex derivative); stearic acid and stearyl alcohol; butylene glycol and propylene glycol, cyclomethicone (volatile silicone); glycerin. Emulsifiers can also be incorporated: glyceryl monostearate (also pearlescent agent); lauramide DEA; or polysorbates.

The class of oils and fatty acids can be subdivided into well-defined families according to their structure, such as: a) saturated fatty acids; b) monoenoic acids; c) polyenoic fatty acids (e.g., methylene-interrupted polymethylene-interrupted, conjugated or allenic acids); d) branched-chain fatty acids (methyl, methoxy or hydroxy), e) ring-containing fatty acids (e.g., cyclopropane, cyclopentenyl, furanoid, cyclohexyl, expoxy, or lipoic acids); f) acetylenic fatty acids; g) hydroxyl fatty acids; h) sulfur-containing fatty acids; i) dicarboxylic acids; j) fatty acid amides; k) methoxy fatty acids; l) keto fatty acids; and m) halogenated fatty acids (F, Cl, Br). (See reference, http://www.cyberlipid.org/fa/acid0001.htm)

In other embodiments, the activating agent could be selected from thixotropic materials, such as certain gels or other solid or semi-solid matter, which undergo a reduction in viscosity or liquefies when subjected to a stress such as being shaken, stirred or otherwise mechanically disturbed, and then solidify again when left standing. Once activated a liquid is preferably combined to ensure further elution through the indicator panel and prevent the thixotropic material from resolidifying. Examples of suitable thixotropic materials may include fumed silica (e.g., also known by the brand names Cabosil® and Aerosil®), a synthetic magnesium phyllosilicates (e.g., Laponite), alumina sols (e.g., Aluminasol, Nissan Chemical America, Houston, Tex.), or a highly-branched polyacrylate polymer.

Section IV.—Manufacturing Method

Figure 9:
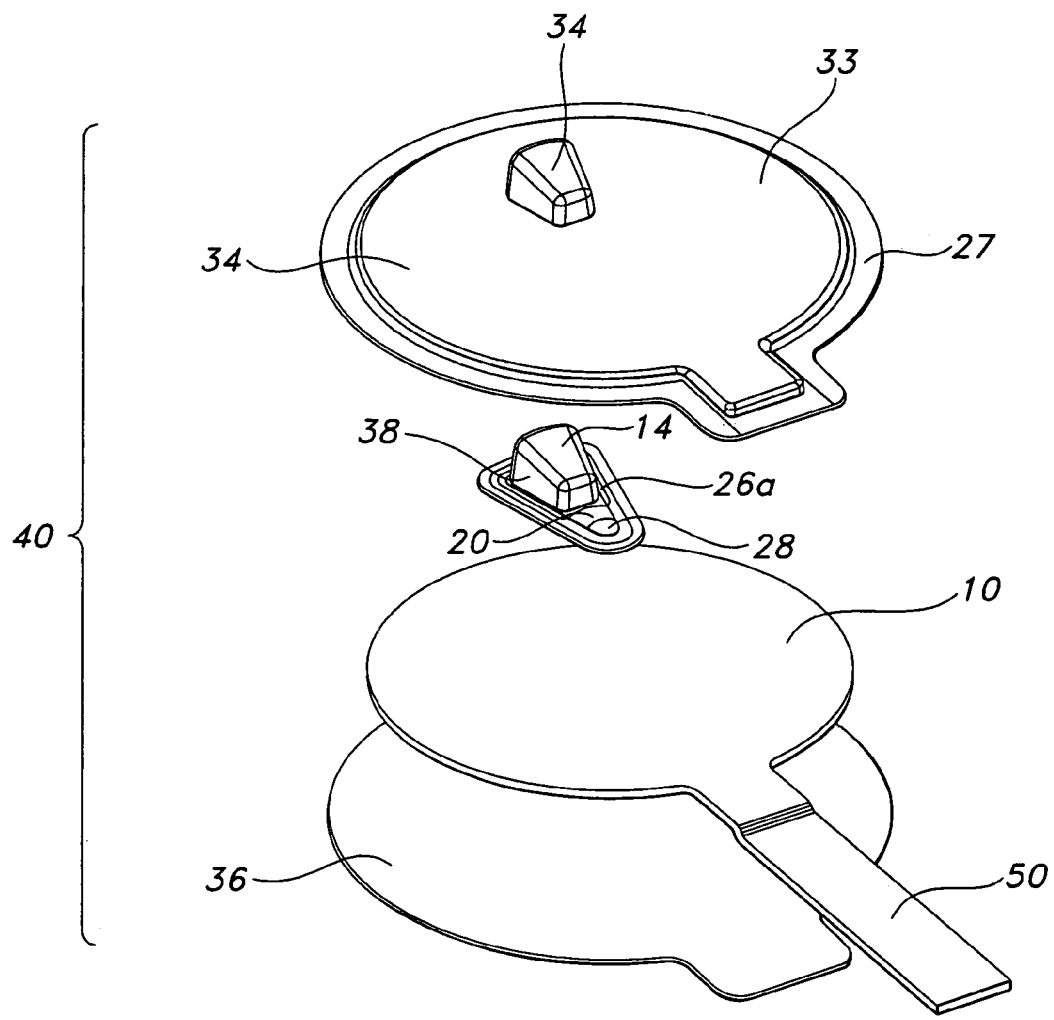
FIG. 9 is an exploded, perspective view of the embodiment of FIG. 8.

One approach or method for manufacturing the present time indicator device may include the following general steps for creating a sealed system. First, form an envelope or containment structure 30 for an indicator panel 10 by placing the indicator panel 10 inside a clear, transparent, first enclosure component 32. According to certain embodiments, this first enclosure component may form the entire envelope (e.g., see FIG. 4), or it may be one part (i.e., a cover) of a two or multiple part containment structure (e.g., see FIG. 9). The enclosure component 32 desirably have a transparent window 33 that is large enough to enable one to clearly view the indicator. The enclosure may be constructed from a variety of materials, such as laminated card-stock, metallic sheets or forms (e.g., aluminum, steel, or tin), polymer plastics (e.g., a transparent self-sealing film, sheath, sleeve, plastic bag or tubing), or glass materials (e.g., tempered tubing or lamp work). Alternatively, a clear cover 34 can be placed against a backing 36 with the indicator panel 10 positioned in between, such as illustrated in FIG. 9, according to an iteration of the present invention. Second, a secure seal 26 is formed around the edges 27 of the plastic or glass cover and backing 36 to enclose the indicator panel 10 within. For embodiments made from plastic materials, heat sealing can create a form-fitting plastic cover over the indicator. Third, provide or form a second enclosed vessel or cell 38. This second enclosed cell 38 will become the reservoir for an activating agent, when an amount of an appropriate or desired activating agent (e.g., a liquid—water, alcohol, aldehyde, ester, ether, ketone, surfactant, or a gas—oxygen, nitrogen, helium, carbon dioxide) is introduced and subsequently sealed within. The cell should be made from a suitable plastic or glass material that will not react with the activating agent. Once sealed the cell becomes an isolated reservoir, until the activating agent released. The second cell 38 is joined to the first containment structure 30 at a location proximal or adjacent to the indicator panel 10. The reservoir cell 38 and indicator panel containment structure 30 together constitutes what is referred to as a housing unit 40. The housing unit can have either a rigid or a semi-pliable, flexible structure.

Any suitable kind of sealing mechanism may be employed to ensure that the contents of the two enclosures cannot escape from the housing and exterior environmental conditions cannot contaminate or disturb the interior of the housing. It is desirable that the contents of the envelopes are not damaged during the sealing process. Commonly, ultrasonic welding, stamp/pressure, or heat sealing techniques for working with either polymer plastic materials or glass, or a combination can be practiced for sealing the units. For instance, to construct a glass enclosed envelope, one can use frit with a suitable coefficient of thermal expansion as the sealant to join a glass cover to a either a glass, ceramic, or metallic substrate that serves as the enclosure backing.

As depicted in the accompanying FIGS. 2-9, continuous, spot, or seamless welds are desired to seal the indicator pane in its protective enclosure. Desirably, the seals are hermetic. In rectilinear-shaped embodiments the seals are hermitic along three-sides, with the fourth side being frangible and joined to the reservoir, such as in FIG. 2, 4, or 7. In round, scalloped, or elliptical shapes, like shown in FIG. 3, 8, or 9, the reservoir is likely to be located at or near the center of the unit, so a hermetic seal 26a closes the entire outer edge. Of course, other or different combinations are also possible, such as a reservoir 14 situated along an outer edge 27 of a rounded form, as depicted in FIG. 6. An adhesive may also work, but consideration should be given to possible contamination or undesired interaction between the adhesive with the mobile phase when the device is activated. The seal 20 formed between the containment structure 30 that houses the indicator panel and the reservoir cell 38 is frangible, as compared to the other seals around the edges of the envelopes that are not. The frangible seal allows for activation of the device by using pressure to break the frangible seal, which opens communication between the two envelopes and forces the activating agent onto the indicator panel. In the embodiment shown in FIGS. 8 and 9, a small aperture or conduit 28 is located next to the reservoir 14 containing an activating agent 12. The activating agent 12 can exit the reservoir 14 through this small aperture 28 and interact with the large indicator panel 10, since the aperture 28 is centered over the large indicator panel 10.

The preceding method can be repeated multiple times to fabricate as many reservoir and indicator housing units as one may desire. Individual housing units may be bundled or joined together to have a number of chromatographic timer indicators in parallel. As illustrated, according to one version, the chromatographic stationary phases can each be within their own separate channel on a presentation, such as a poster-sized board. A timer of such a large configuration can be hung on walls and could be seen from a distance. Such large chronographs may be used as timing devices on industrial shop floors or for examination takers to see from a distance.

Since the present chronograph device can be manufactured relatively inexpensively, one-use or disposable models are envisioned according to certain embodiments.

Section V.—General Applications for the Indicator Chronograph

The present timing device can be tailored to develop over any predetermined time frame and for any type of application in which one would need to monitor time; hence a universal indicator for all ages and activities. The present invention can be used in a number of formats and adapted for various applications, for example, clinical uses to food and beverage related monitoring to hygiene training. The chronograph can function as a stand-alone indicator device or it can be combined with or incorporated in another article. The chronograph may be included in an assembly or kit with or attached to other items that may have time-dependent or time-influenced functionality or use.

The time indicator can be a disposable, self-contained tool, which can be used in virtually any environment where a timer for a specified duration is appropriate, without fear of temperature or other external factors affecting its function. The device also can be used as a training aid or tool to reinforce or condition one to perform certain activities. For instance, with young children who are potty-training, the gradual change in color of the timed indicator can help motivate them to stay dry over an ever longer duration. Alternatively, the indicator can help children gain a concept of time, for staying quiet or napping, or the device can be applied towards monitoring hygiene. For instance, as a visual aid for newly menstruating girls to remind them to change a feminine pad or tampon. In both types of applications, the present chronograph device can be adjusted or tuned to develop in a prescribed amount of time, depending on the particular purpose.

The following descriptions serve as illustrative examples of several fields in which the present chronograph may be employed. The present chronograph device could be deployed as a stand-alone device or be part of a package assembly or kit with other articles or components to help in medical or clinical settings, for example: a) as a general timer for patient care, which can unburden the caregiver and put control in the hands of patients, b) a diagnostic tool accompaniment (e.g., monitor any test with a time-dependent development), c) to help patients monitor for how long medication is effective or be cognizant of the time a dosage of a drug was taken or should be taken (e.g., 4-hour dosage times, avoiding over medication), d) setting or treatment timer (e.g., bone cement, plaster, dental adhesive, whitening treatment or when to wash off skin treatments, etc.), e) timer for wound dressing changes or draining, or f) as a patient waiting-time monitor.

Furthermore, one can employ the chronograph indicator in food-related areas, such as a freshness indicator for the length of time something (e.g., coffee, baked goods, deli goods, vegetables/produce, buffet or fast food, airline food, or other products) has been stored or sitting, or a delivery timer for guaranteed delivery times. Beverage-related uses may include individual alcohol drink timers (i.e., 1 drink/hour is recommended)—the drinker starts the timer when he or she begins drinking, which also can be a promotional tool at bars or nightclubs; a "flatness" indicator for carbonated beverages (soda, beer, etc.)—start timer when the beverage container is first opened and the beverage maker can dictate how long before the drink goes "flat"; and a timer for allowing red wine to breath—chronograph can hang on the wine bottle to indicate when breathing time is sufficient.

Similarly, the visual chronograph can also be used for or packaged with cosmetic or health care products and applications. For instance, the chronograph can monitor the duration of a hair care or skin care application or treatment (e.g., perms, colorants, facials, topical treatment, bleaching, etc.), or could be used as a guard against over exposure in a spa environment, such as in hot-tubs or saunas. Also, the chronograph can be used by hobbiests as a timer for applying etching solutions, paint remover, glue setting, or to monitor mixing times (e.g., epoxy, paint, etc.).

The present invention provides a noiseless, silent timer device. The chronograph can serve as a child-friendly timer for monitoring, for example, sun exposure (e.g., when to apply or reapply sun screen, or when to get out of the sun), length of television watching, length of playtime or time-outs, or any other situation in which one can't or it may be inconvenient to tell time. In schools, as mentioned previously, a larger version of the chronograph could be used as an examination timer.

The present chronograph device can serve as an indicator for environments where moisture content is critical. For example, as meat ages, it gives off liquid. An indicator with both the timed portion and the wetness indicator could be built into packaging and is designed to develop once a certain liquid level in the package has been reached, providing the customer with a visual indicator of the age of the meat. According to a similar concept, as will be further discussed, the present chronograph can be adapted and integrated into various personal care products, such as diapers, child training pants, or adult incontinence items and other similar types of articles or garments to serve as a wetness/dryness indicator.

Section VI.—Wetness/Dryness Indicator Uses

As a further application of the present invention, the chronograph and its visual indicator can be used to monitor either the maintenance of dryness and/or the presence of wetness to ensure insult-free wear or use of either a personal care product (e.g., a diaper, adult care garments), or an absorbent article (e.g., a pad used in medical procedures, meat or poultry packaging, or pre-packaged vegetable, moisture detecting). The term "insult-free" refers to the state of the indicator display area or panel being uninterrupted or undisturbed in the development or progress of the mobile phase of the activating agent as it traverses the display area. When an "insult" occurs, the development or progress of the activating over the display area is either disturbed, deactivated, or destroyed. In other words, the pattern or design which the activating agent generates can be altered, stopped, or completely negated, but not reset.

A practical application of the present color-coded moisture indicator can be employed in the conditioning and training of children, in general, and for potty training in particular. For instance, the indicator may be incorporated as part of a training pant for conditioning a child to develop bladder control by providing a positive feedback when the child remains dry for an extended period of time (e.g., 2-4 hours, or 3-6 hours). As such, the chronograph can be both a child-friendly and child-appropriate timing device.

Children of potty training age usually cannot tell time using a conventional timing device, such as a clock. Such young children, however, do have a well developed ability to recognize visual changes. Hence, the present invention can be employed as a training aid for children. The device takes advantage of the child's visual skill development to achieve a training goal with a visual representation of the amount of time elapsed. The child can be encouraged to maintain dryness for a given period of time, the length of which can increase as the training progresses and the child's self-control increases.

At the present, few, if any, products on the market can provide a positive feedback mechanism for children who are of potty training age, even though providing positive feedback is strongly encouraged by the majority of training programs. (See B. Spock, M.D., and M. B. Rothenberg, M.D., *Dr. Spock's Baby and Child Care*, 6th Ed., pp. 457-475, ISBN: 0-671-75967-1, Pocket Books, 1992; or Wall Street Journal, "*Un-Pampered: Tots Face Strict Deadline on Toilet Training*," pp. A1, A6, Aug. 27, 2004.) To meet this need, we have developed, according to one iteration of the present invention, a wetness/dryness indicator.

Potty training a young child typically includes a wide variety of different aspects, including many training techniques and training aids that may be useful to parents and caregivers, hereinafter referred to simply as caregivers. One feature of potty or toilet training is having the young child change from wearing diapers to wearing training pants to help the child understand that he or she should now use the commode just like adults. An additional feature of the potty training process includes caregiver instruction and feedback as a positive encouragement and reinforcement to the child that he or she should now be using the toilet instead of diapers. Although the use of training pants and positive encouragement or feedback from caregivers has been helpful and is recommended for the training process, there still is room for improvement in providing more positive feedback mechanisms. Specifically, caregivers continue to search for alternative reward systems to guide their children successfully through the potty training process.

As a general consensus among child rearing experts, and as described in various parenting guides, positive reinforcement is preferred for training or conditioning a child to an activity. For example, when potty training, positive feedback can be a valuable training tool, which aides in the conditioning of self-control. It is envisioned that when applied to the outside of a personal care product, such as children's training pants, the chronograph can provide the child a greater feeling of control and ownership in the child's potty training efforts, at an age where the child wishes to assert his or her independence. This, in turn, contributes to a positive feedback system of reward or affirmation for the child, which can motivate the child to try to maintain dryness for longer periods. It is envisioned that the present invention can be adapted to be a tool that can provide or instill a sense of empowerment or independence in a child by providing the child with the ability to supervise or control over his or her own behavior.

Moreover, a problem facing caregivers is that they do not always know when a child has had an accident in his or her training pants, the knowledge of which can help in the potty training process since the accident will be still fresh in the child's mind. Conventionally, wetness indicators have been used as a mechanism to assist the caregivers in knowing when the article has been wetted or soiled. Conventional wetness indictors of this sort tend to be complex., whether they involve disappearing inks, appearing inks, inks activated by heat, or rely on body chemistry or pH indicators and the like, etc., to work. The present invention, in contrast, can be adapted to be a dryness indicator without the need to rely upon complicated chemical interactions.

Further it is known that caregivers sometimes have difficulty determining whether or not a personal care products, such as a diaper on a baby or adult incontinence garments on cognitively disabled persons is wet or dry without disturbing the wearer, and if the wearer is asleep, they may be awakened inadvertently. Accordingly a personal care product which is capable of providing a readily visible signal when wet and in need of changing is highly desirable. A quick glance at the visual indicator panel will permit a caregiver to determine for how long the device has been activated. This feature of the present invention may be employed in a variety of applications. For example, once the indicator is activated, a quick inspection of the indicator panel can tell a caregiver the status for how long a child has gone without urinating and also allows the child him or herself to see by color zones, how long they have remained dry. This serves as a positive feed-back training tool. That is, in some embodiments a picture or pattern develops to reward the child for staying dry. In contrast, conventional potty-training aids often use a negative feedback, by which if a child wets himself, for example, the initial picture or design on the training pants either changes from a happy image to a sad image or disappears all together.

As a training aid for children during potty training, it is envisioned that the present chronograph can be formed as part of diaper or other a personal care product itself or as an add-on that can be purchased separately. The indicator would be activated once the caregiver has put the diaper on the child. Initially as potty training begins, the target or predetermined development time would be for about 2-3 hours. As the child's ability to exercise self-control improves, the caregiver can increase the duration with other indicators designed for longer development times (i.e. 4-5 hours, or 8 hours for overnight use). Ideally, the indicator would contain some time markers so that caregivers could estimate, for example, at what point during the night the child wet his or her diaper—either closer to the time the child went to bed or closer to the time the child wakes.

The indicator may have either monochromatic or multi-colored zones along the indicator panel to display the time elapsed. In monochromatic versions, when each zone contacts or reacts with the activating agent, a visual signal is set or marked off. In multicolored embodiments, each zone has a different color, which provides a simple visual color feedback of the time duration. The boundaries of each of the colored zones on the indicator panel may correspond with a set amount of time, or each colored zone be divided into a certain number of subsections by markings which indicate both distance and indirectly the amount of time that passes. In other words, an observer will be able to track the progression of visual change or development by following the spatial development of either a change in color or design, or other visual manifestation or signal, since each of the marking signify a certain predetermined increment of time.

When incorporated into certain articles, such as personal care products, the indicator may be used either to monitor the passage of time, check for the absorbency and wicking properties of an article, for the presence of dryness and/or the absence of moisture over time, or as a training tool that can provide a positive feedback.

According to an embodiment, a number of colored regions or stripes of colorant are situated on a simple cellulose-based wicking strip that is sealed in an envelope or enclosure to provide the visual signal or indication on for the indicator display area. Using food dyes (e.g., FD&C yellow 5, blue 1, and red 4) a series of colored stripes is created on a 10-20 cm long strip of wicking material. The strip is marked at predetermined intervals to delineate the distance the activating agent front will travel over a given period of time, or also referred to as timed zones. The wicking strip is sealed in a tight-fitting envelope with at least one surface being clear and transparent. The transparent window allows one to observe the colored stripes. Adjacent to the envelope containing the colored wicking strip, is a reservoir containing an activating agent. When a frangible seal between the envelope and the reservoir is ruptured, communication between the two is established. The activating agent can enter into the envelope and trigger the colored indicator strip. For instance, when a mobile phase, such as water, wicks along the strip, and comes into contact with the colors in each strip, the fluid front will carry the color forward across the strip. As the color dye of a first stripe contacts the dye of the next adjourning colored stripe, the two dyes will mix.

The breaking of the frangible seal can be done by either a caregiver or a child to start the timed indicator into action. The entire wicking processes, from one end of the colored strip to the other, can be designed to take from about 2-4 or 6 hours, based on the materials used and conditions set. Non-water soluble ink lines may act as filters or dams, which slow down the flow.

According to an embodiment, the present chronograph indicator has a timed display panel portion that may be combined with a second indicator that can sense the presence of moisture and disrupt the timed portion, generating a visual cue to the user and/or caregiver that an accident has occurred. The second indicator can be, in certain embodiments that employ a conduit, a second wicking strip which interacts with the time indicator panel. The length of the wicking strip is limited by the size of the absorbent article (e.g., diaper or pad). The conduit should be sufficiently long enough to reach from the absorbent core to the waistband of the diaper, and the narrowness is probably limited by the amount of dye necessary on the interference or disruptor to generate a strong marking or visual effect. In certain examples, the present designs are tested with about 1 ml of water to simulate an urination event. It is believed that a narrower piece of material will require less moisture to complete the wicking process. This amount is sufficient to cause disruption of indicator development. That would probably be significantly lower than normal amount of urine that is released during an event and probably mimics the "partial release" concept better than a full release. A partial release is the kind of release one would actually want to monitor during potty training to achieve the desired goal.

To illustrate, an execution of the present invention shown in FIGS. 5A-D. Timed visual indicator strips were generated using wicking materials and FD&C approved dyes (yellow 5, red 4 and blue 1). Wicking strips were cut into the desired length (~4-4.5 inches) and the desired width (~0.5-1 inch). The dye solutions (50 mg in 10 ml of water) were striped onto the wicking material (0.02-0.04 ml). A second wicking strip 50 functions as a conduit for an interference agent or disruptor mechanism. The second strip can be prepared with a line or zone of dark ink 51 (e.g., brown or black) placed on it. The dark ink acts as an interference agent or disruptor of the time indicator when the presence of moisture is sensed. In the example at hand, the second strip was prepared by loading a black dye (0.04 ml) onto an end of the second strip 50, as shown in FIG. 5A. One or a plurality of different secondary strips 50 can be placed in contact with or attached to the primary indicator strip at different positions along the colored strip's length; or if a circular or round-shaped embodiment, around its perimeter. Moisture moving up the second trip will carry the dark colored ink into the first indicator strip. FIG. 5B shows the secondary wetness indicator strip 50 with the dark colored ink or dye 51 placed in a perpendicular manner adjacent to the primary, colored indicator strip 10. Both the second disruptor strip and the primary indicator strip are encased in a plastic sheath. When an source of moisture (e.g., water or urine) moves through the second wetness strip, the dark dye is carried up onto the primary timed indicator strip, disrupting the progress of color development and providing feedback to the user. Embodiments of the present concept is shown in FIG. 6, alternative configurations are shown in FIGS. 7 and 8.

In another variation, the indicator strip can have a plurality of ionic gates, such as described above, or a variant of "colorant or dye-capturing" barrier lines oriented largely perpendicular to the direction of mobile phase elution. These barrier lines contain agents that bind to the dyes and halt the further progress of the dye past these lines. In certain examples, the barrier lines can be formed with polycationic polymers with either a positively or negatively charged moiety on each monomer unit allowing for the capture of the oppositely charged dye or colorant moiety. Examples of such polycationic polymers or oligomers are: polyethyleneimine, MW 800-1MM (Polysciences Inc., PA), aluminum chlorohydrate, aluminum nanoparticle (e.g., Snowtex-AK and aluminasol (Nissan Chemical America, Houston Tex.)), polyethyleneimine, and its permethylated or perbrominated salts (Polysciences Inc., PA). Examples of anionic oligomers and polymers include: polyvinylsulfonic acid (Polysciences Inc., PA). Examples of neutral dye trapping agents include: cyclodextrin (e.g., Alpha, Beta and Gamma) available from Cerestar (Hammond Ind.), starch, or silica. As most dyes are negatively charged, due the presence of the sulfonic acid or carboxylic acid groups, they readily bind to the positively charged, polycationic lines that have been fixed on the indicator substrate. It is envisioned that in a working device with barrier lines, when a mobile phase carrying a first color along the strip reaches a first barrier line, the color molecules are halted at the line, while the mobile phase continues past the line uninhibited. The mobile phase continues and comes in contact with a second color which then wicks along with the mobile phase front, until it reaches another barrier line. In this manner separated or segregated sections of vivid colors are generated according to one iteration of the invention.

In such a design, the indicator panel can be designed to show or indicate the proximal point of time when wetness occurred. The barrier lines can control the direction that a disrupter dye elutes and confine it to an unidirectional progress away from the original starting point of the timed indicator panel. In other words, the barrier lines can prevent a disrupting dye, once it comes in contact with the timing element, from flowing backward toward the activating agent reservoir and destroying the vivid colored regions that have already developed before the onset of wetness. To illustrate, for example, the wetness indicator can be activated by urine or some other liquid, which wicks up the strip, carrying the black dye up onto the colored visual strip, thereby disrupting the vivid color(s). Disruption of the colored strip at a certain time point provides a feedback message to the wearer or caregiver. The actual zone of wetness can be identified by observing at which point or zone of color generation on the indicator strip the black dye migrates into. Those zones that remain either colorful or undeveloped, can indicate respectively the time periods before and after the assault of wetness.

Integration of a version of the present chronograph device indicator with personal care applications for infants or older children may easily be extended to incontinence monitoring for adult care, such as for persons of any age who may have diminished capacity to control certain bodily functions. For instance, the present device can be useful to caregivers or those who may have lost the ability to tell time when suffering from dementia, such as advanced stages of Alzheimer's Syndrome, and must be either retrained or reminded. The present invention can help address the need and demand of caregivers for a conspicuous indicator of wetness in diapers and incontinence products. An integrated indicator could provide a visual cue to caregivers of in hospital nurseries as well as nursing homes or other long-term care environments where there are numerous residents that require attention. This would provide conspicuous, quick feedback for caregivers and an additional method of communication for the user.

For personal care products such as diapers, children's training pants or adult incontinence items, a disruptor in the product can be triggered for release into the indicator display panel at the moment that a substantial or significant amount of wetness or moisture is first detected. The absorbent area in a personal care product or garment, according to some embodiments, can have a sensitivity or tolerance level for as little as about 0.5 ml to trigger the disrupter. More commonly, the absorbent area can have a trigger as sensitive as about 1-2 ml, a typical, minimal volume amount of liquid release by the child in a wetting accident—not to mention any amount of up to about 1 liter. When the disrupter reaches the display panel, the disrupter creates a mark on the display panel to show the point in time when the moisture level reached a detectable limit. The disruptor can either stop further progression of the mobile front and therefore development across the indicator display, or it can cause the design or pattern that was developing to change or disappear. Various suitable pigments, inks, or dyes can be useful in generating the markings which signal a disruption of display pattern development by an alternate moisture or wetting source have been already described herein.

As an example of other fluids, for children's training pants or adult incontinence products, urine itself may function as an interrupting agent in a second mobile phase, which disrupts or arrests the development of the indicator. In the case of children's training pant applications, introduction of the disruptor on the display panel allows the child and his or her caregiver to quickly observe the length of time that the child was able to maintain dryness, at what time the child wet himself, and whether or when the child needs changing. Complete development of the indicator panel is designed to be a positive feedback mechanism for the child and to motivate the child to keep dry, thereby reinforcing the potty training concept of long-term dryness. A second disrupter mobile phase can be oriented to intersect with the initial activating agent mobile phase. In the situation of a training pant, using similar principles as the indicator panel development, the second mobile phase (urine) wicks up a strip from the absorbent diaper core once the child wets and carries the dye on the disruptor strip onto the indicator panel simply through directional flow. For example, in monochromatic or bi-chromatic indicator panels, an entirely or segmented yellow-dye colored strip can form the indicator and addition of a blue dye as the disrupter, will mix and generate a green signal when the child wets. Similarly, in the case of adult incontinence items, a caregiver can note at a glance the duration that the incontinence item has been worn and whether the patient needs to be changed.

It is contemplated that the present invention in addition to being used for child or adult care incontinence articles can be adapted and incorporated into a variety of diverse products and articles for different applications. For examples, the chronograph may be used as to monitor the length of time the article has been worn or used. The device may be an indicator in a glove, surgical or medical gowns, drapes, bandages or dressings.

The present invention has been described in general and in detail by way of examples. Persons of skill in the art understand that the invention is not limited necessarily to the embodiments specifically disclosed, but that modifications and variations may be made without departing from the scope of the invention as defined by the following claims or their equivalents, including other equivalent components presently known, or to be developed, which may be used within the scope of the present invention. Therefore, unless changes otherwise depart from the scope of the invention, the changes should be construed as being included herein.

We claim:

1. A chronograph comprising: an indicator panel having a region with a number of visually distinct sections arrayed spatially relative to each other, said visually distinct sections each having at least one colorant different from an adjacent section, and having at least a reservoir containing an activating agent that constitutes a mobile phase that interacts with said indicator panel, and which transports said colorant along said indicator panel at a rate less than a rate of progression of said mobile phase for monitoring relative passage of time, and said reservoir being in controlled communication with said indicator panel.

2. The chronograph according to claim 1, wherein said indicator panel is enclosed in a housing unit having at least a portion that is clear or transparent for observing said indicator panel.

3. The chronograph according to claim 1, wherein said indicator panel is either a substantially two-dimensional visual display or is part of a three-dimensional shaped surface or article.

4. The chronograph according to claim 1, wherein at least part of said indicator panel is composed of a cellulose-based material, a gel, a plastic/polymer film, chromatographic separation materials, inorganic particles or oxides, or combinations of such materials.

5. The chronograph according to claim 1, wherein said reservoir contains an activating agent.

6. The chronograph according to claim 5, wherein said activating agent is a fluid.

7. The chronograph according to claim 6, wherein said fluid is either a gas, a liquid or, a gel.

8. The chronograph according to claim 7, wherein said liquid is either water, a thixotropic material, an alcohol, a solvent, or other organic species.

9. The chronograph according to claim 8, wherein said organic species is non-flammable.

10. The chronograph according to claim 8, wherein said organic species is a surfactant, a fatty acid, or an aliphatic alcohol.

11. The chronograph according to claim 7, wherein said gas is either air, oxygen, carbon dioxide, a reducing gas, an inert gas, a moist gas, or a mixture thereof.

12. The chronograph according to claim 1, wherein said visually distinct sections are colored.

13. The chronograph according to claim 1, wherein said visually distinct sections are arrayed either adjacent to each other or spaced apart.

14. The chronograph according to claim 1, wherein said colored sections are either monochromatic or include different colors.

15. The chronograph according to claim 1, wherein said device further includes a frangible seal between said reservoir and said indicator panel.

16. The chronograph according to claim 15, wherein said timing element is activated when said frangible seal is broken, establishing communication between said reservoir and said indicator panel.

17. The chronograph according to claim 1, wherein said activating agent elutes at a predetermined rate as a mobile phase front either on or within a surface of said indicator panel.

18. The chronograph according to claim 17, wherein said predetermined rate is calibrated as a unit of distance per unit of time, on order of either minutes, hours, or days.

19. The chronograph according to claim 1, wherein said device further includes an interference agent adapted to disrupt development of said timing element.

20. The chronograph according to claim 19, wherein said interference agent is a mobile phase that effectively elutes or disrupts development of said timing element.

21. The chronograph according to claim 19, wherein said interference agent is either hydrophilic or hydrophobic to arrest said timing element development.

22. The chronograph according to claim 20, wherein said interference agent is either a colorant, dark colored dye, an alternate source of moisture, water, solvent, or urine.

23. The chronograph according to claim 19, wherein said interference agent modifies a visual appearance of said indicator panel indicating a change in conditions.

24. The chronograph according to claim 23, wherein said change in conditions involves the occurrence of an insult.

25. The chronograph according to claim 1, wherein said indicator panel is adapted to monitor duration of dryness.

26. The chronograph according to claim 1, wherein said chronograph has a display with a size that ranges from an object that is capable to be held within an average person's hand to an object as large as a billboard.

27. A self-timing article having a chronograph for monitoring the duration over which said article has been applied or used, the chronograph comprises: a set of visually distinct zones arrayed spatially relative to each other on a display region of said chronograph, and having a self-contained reservoir containing an activating agent that constitutes a mobile phase that interacts with said indicator panel, and which transports a colorant along said indicator panel at a rate less than a rate of progression of said mobile phase that manifests on said indicator panel progressively over time as said activating agent migrates from said reservoir across said display region.

28. The self-timing article according to claim 27, wherein said timing element manifests on said display region until interrupted by an introduction of an alternate source of moisture or wetness.

29. The self-timing article according to claim 28, wherein introduction of said alternate source of moisture generates a marking on said display region that signifies relative time when said introduction occurred.

30. An assembly comprising: a chronograph having an indicator panel, said indicator panel having a region with a number of visually distinct sections arrayed spatially relative to each other, and having at least a reservoir containing an activating agent that constitutes a mobile phase that interacts with said indicator panel, and which transports a visually distinct species along said indicator panel at a rate less than a rate of progression of said mobile phase for a timing element that manifests on said indicator panel to monitor relative passage of time, and said reservoir being in controlled communication with said indicator panel.

31. The assembly according to claim 30, wherein said assembly includes other component items that may have time-dependent or time-influenced functionality or use.

32. The assembly according to claim 30, wherein said indicator is either a stand alone article in said assembly or can be incorporated as part of a component of said assembly.

* * * * *